US010766940B2

United States Patent
Jhamandas et al.

(10) Patent No.: US 10,766,940 B2
(45) Date of Patent: Sep. 8, 2020

(54) BRAIN PENETRANT AMYLIN RECEPTOR BASED PEPTIDES FOR ALZHEIMER'S DISEASE

(71) Applicant: The Governors of the University of Alberta, Edmonton (CA)

(72) Inventors: Jack Jhamandas, Edmonton (CA); Rania Soudy, Edmonton (CA); Kamaljit Kaur, Edmonton (CA); Wen Fu, Edmonton (CA); David MacTavish, Edmonton (CA); Aarti Patel, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 15/705,789

(22) Filed: Sep. 15, 2017

(65) Prior Publication Data
US 2018/0134763 A1 May 17, 2018

Related U.S. Application Data

(60) Provisional application No. 62/396,370, filed on Sep. 19, 2016.

(51) Int. Cl.
| | | |
|---|---|---|
| *A61K 38/00* | (2006.01) | |
| *C07K 14/575* | (2006.01) | |
| *A61P 25/28* | (2006.01) | |
| *C07K 14/585* | (2006.01) | |

(52) U.S. Cl.
CPC ............ *C07K 14/575* (2013.01); *A61P 25/28* (2018.01); *C07K 14/585* (2013.01); *A61K 38/00* (2013.01)

(58) Field of Classification Search
None
See application file for complete search history.

(56) References Cited

U.S. PATENT DOCUMENTS

| | | | | | |
|---|---|---|---|---|---|
| 5,580,953 | A | * | 12/1996 | Albrecht ............... | C07K 14/575 530/303 |
| 2014/0329752 | A1 | * | 11/2014 | Soares ................. | C07K 14/585 514/11.9 |

OTHER PUBLICATIONS

Abedini A, Schmidt AM. Mechanisms of Islet Amyloidosis Toxicity in Type 2 Diabetes. FEBS letters. 2013;587:1119-27.
Ahmed S, Mathews A, Byeon N, Lavasanifar A, and Kaur K. Peptide Arrays for Screening Cancer Specific Peptides, Anal. Chem., 2010, 82 (18), 7533-7541.
Banks WA, Kastin AJ, Maness LM, Huang W, Jaspan JB. Permeability of the blood-brain barrier to amylin. Life Sci. 1995;57:1993-2001.
Banks WA, Kastin AJ. Differential Permeability of the Blood-Brain Barrier to Two Pancreatic Peptides: Insulin and Amylin. Peptides. 1998;19:883-9.
Bateman RJ, Xiong C, Benzinger TLS, Fagan AM, Goate A, Fox NC, et al. Clinical and Biomarker Changes in Dominantly Inherited Alzheimer's Disease. N Engl J Med. 2012;367:795-804.
Chishti MA, Yang D-S, Janus C, Phinney AL, Horne P, Pearson J, et al. Early-onset Amyloid Deposition and Cognitive Deficits in Transgenic Mice Expressing a Double Mutant Form of Amyloid Precursor Protein 695. J Biol Chem. 2001;276:21562-70.
Danysz W, Parsons CG. Alzheimer's disease, β-amyloid, glutamate, NMDA receptors and memantine—searching for the connections. Br J Pharmacol. 2012;167:324-52.
Davey RA, Turner AG, McManus JF, Chiu WSM, Tjahyono F, Moore AJ, et al. Calcitonin Receptor Plays a Physiological Role to Protect Against Hypercalcemia in Mice. J Bone Miner Res. 2008;23:1182-93.
Di L. Strategic Approaches to Optimizing Peptide ADME Properties. The AAPS Journal. 2014;17:134-43.
Di Pardo A, Maglione V, Alpaugh M, Horkey M, Atwal RS, et al (2012) Ganglioside GM1 induces phosphorylation of mutant huntingtin and restores normal motor behavior in Huntington disease mice. Proc Natl Acad Sci USA 109(9):3528-3533.
Edvinsson L, Goadsby PJ, Uddman R. Amylin: Localization, Effects on Cerebral Arteries and on Local Cerebral Blood Flow in the Cat. ScientificWorldJournal. 2001;1:168-180.
Fu W, Ruangkittisakul A, MacTavish D, Shi JY, Ballanyi K, Jhamandas JH. Amyloid β (Aβ) Peptide Directly Activates Amylin-3 Receptor Subtype by Triggering Multiple Intracellular Signaling Pathways. J Biol Chem. 2012;287:18820-30.
Han L, Huang R, Liu S, Huang S, Jiang C. Peptide-Conjugated Pamam for Targeted Doxorubicin Delivery to Transferrin Receptor Overexpressed Tumors. Mol Pharm. 2010;7:2156-65.
Hardy J, Selkoe DJ. The Amyloid Hypothesis of Alzheimer's Disease: Progress and Problems on the Road to Therapeutics. Science. 2002;297:353-6.
Hardy J. The amyloid hypothesis for Alzheimer's disease: a critical reappraisal. J of Neurochem. 2009;110:1129-34.
Hay DL, Christopoulos G, Christopoulos A, Poyner DR, Sexton PM. Pharmacological Discrimination of Calcitonin Receptor: Receptor Activity-Modifying Protein Complexes. Mol Pharmacol. 2005;67:1655-65.
Hay DL, Poyner DR, Sexton PM. GPCR modulation by RAMPs. Pharmacol Ther. 2006;109:173-97.

(Continued)

*Primary Examiner* — Olga N Chernyshev
(74) *Attorney, Agent, or Firm* — Rudy J. Ng; Bozicevic, Field & Francis LLP

(57) ABSTRACT

Amylin receptor antagonists capable of binding to the amylin receptor and inhibiting activity of amylin or amyloid-beta protein are provided. The amylin receptor antagonists can be administered in the form of pharmaceutical compositions or the like. Methods for preparing and using the amylin receptor antagonists for treating, preventing, or ameliorating Alzheimer's disease are also provided.

5 Claims, 23 Drawing Sheets
Specification includes a Sequence Listing.

(56) References Cited

OTHER PUBLICATIONS

Husmann K, Sexton PM, Fischer JA, Born W. Mouse receptor-activity-modifying proteins 1, -2 and -3: amino acid sequence, expression and function. Molecular and Cellular Endocrinology. 2000;162:35-43.
Janus C, Pearson J, McLaurin J, Mathews PM, Jiang Y, Schmidt SD, et al. A[beta] peptide immunization reduces behavioural impairment and plaques in a model of Alzheimer's disease. Nature. 2000;408:979-82.
Jhamandas JH, MacTavish D. Antagonist of the Amylin Receptor Blocks β-Amyloid Toxicity in Rat Cholinergic Basal Forebrain Neurons. J Neurosci. 2004;24:5579-84.
Jhamandas JH, Li Z, Westaway D, Yang J, Jassar S, MacTavish D. Actions of β-Amyloid Protein on Human Neurons Are Expressed through the Amylin Receptor. Am J Pathol. 2011;178:140-9.
Jhamandas JH MD. β-Amyloid protein (Aβ) and human amylin regulation of apoptotic genes occurs through the amylin receptor. Apoptosis. 2012;17:37-47.
Jhamandas JH VV, MacTavish D, Fu W Microglial amylin receptors: a novel target for the actions of beta amyloid (Aβ) protein. Society for Neuroscience Meeting Abstracts 39.01/B88, Chicago, IL USA. 2015.
Kimura R, MacTavish D, Yang J, Westaway D, Jhamandas JH. Beta Amyloid-Induced Depression of Hippocampal Long-Term Potentiation Is Mediated through the Amylin Receptor. J Neurosci. 2012;32:17401-6.
Kimura R MD, Yang J, Westaway D, Jhamandas JH. Pramlintide Antagonizes Beta Amyloid (Aβ)-and Human Amylin-Induced Depression of Hippocampal Long-Term Potentiation. Mol Neurobiol. Jan. 15, 2016. [Epub ahead of print].
Liu Y-H, Giunta B, Zhou H-D, Tan J, Wang Y-J. Immunotherapy for Alzheimer disease: the challenge of adverse effects. Nat Rev Neurol. 2012;8:465-9.
Patel An, Jhamandas JH. Neuronal receptors as targets for the action of amyloid-beta protein (Aβ) in the brain. Expert Rev Mol Med. 2012;14: 14:e2. doi: 10.1017/S1462399411002134.
Roth JD. Amylin and the regulation of appetite and adiposity: recent advances in receptor signaling, neurobiology and pharmacology. Curr Opin Endocrinol Diabetes Obes. 2013;20:8-13.
Selkoe DJ. Normal and Abnormal Biology of the beta-Amyloid Precursor Protein. Annu Rev of Neurosci. 1994;17:489-517.
Selkoe DJ. The therapeutics of Alzheimer's disease: Where we stand and where we are heading. Ann of Neurol. 2013;74:328-36.
Vassar R. BACE1 inhibitor drugs in clinical trials for Alzheimer's disease. Alzheimer's Res Ther. 2014;6:1-14.
Wang H, Abedini A, Ruzsicska B, Raleigh DP. Rationally Designed, Nontoxic, Nonamyloidogenic Analogues of Human Islet Amyloid Polypeptide with Improved Solubility. Biochemistry. 2014;53:5876-84.
Westermark P, Andersson A, Westermark GT. Islet Amyloid Polypeptide, Islet Amyloid, and Diabetes Mellitus. Physiol Rev. 2011;91:795-826.
Wu H, Yao L, Mei J, Li F. Development of synthetic of peptide-functionalized liposome for enhanced targeted ovarian carcinoma therapy. Int J Clin Exp Pathol. 2015;8:207-16.
Zhu H, Wang X, Wallack M, Li H, Carreras I, Dedeoglu A, et al. Intraperitoneal injection of the pancreatic peptide amylin potently reduces behavioral impairment and brain amyloid pathology in murine models of Alzheimer's disease. Mol Psychiatry. 2015;20:252-62.
Author unknown, "2016 Alzheimer's Statistics" [online] [retrieved on Nov. 21, 2017]; retreived from www.alzheimers.net using Internet URL: www.alzheimers.net/resources/alzheimers-statistics; 2016; pp. 1-5.

* cited by examiner

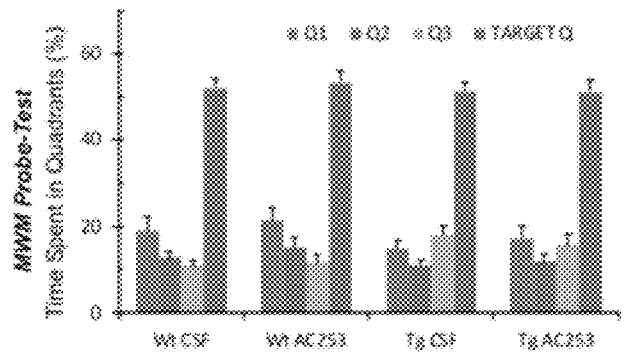
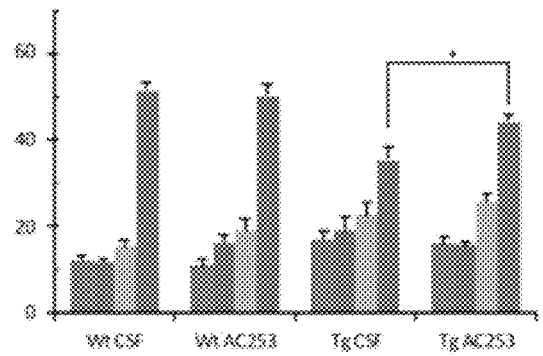
FIG. 2D
FIG. 2E
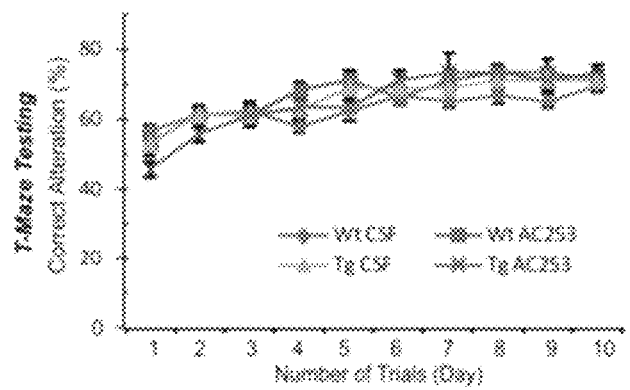
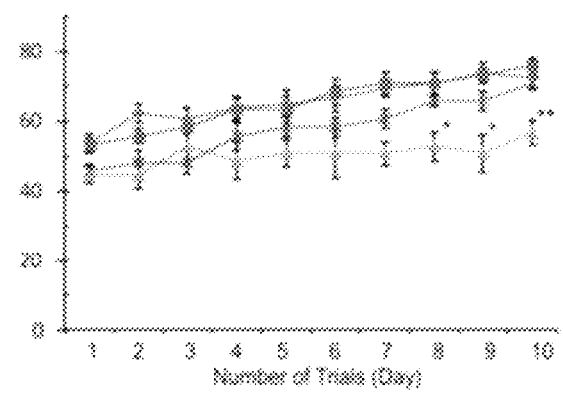
FIG. 2F
FIG. 2G
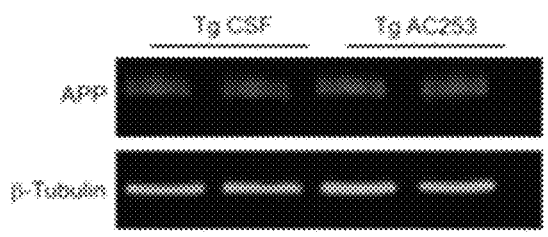
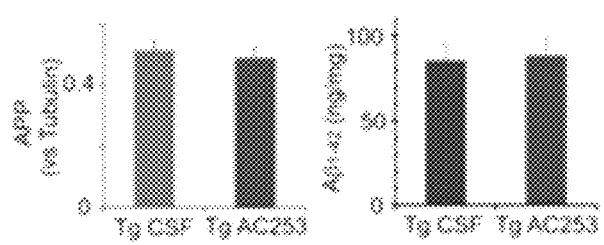
FIG. 3A
FIG. 3B
FIG. 3C

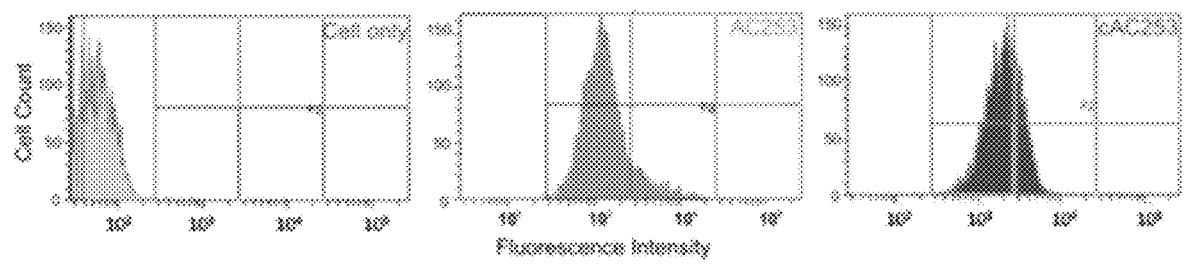
FIG. 6A
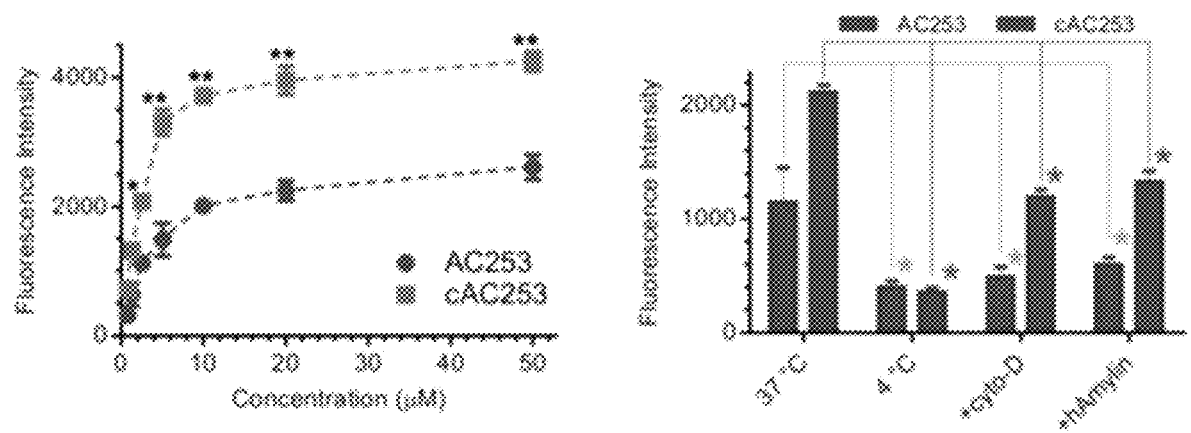
FIG. 6B
FIG. 6C
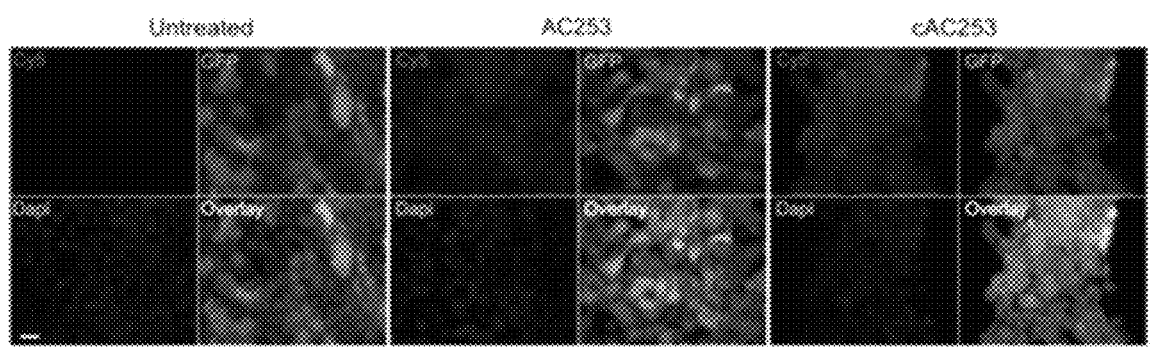
FIG. 6D

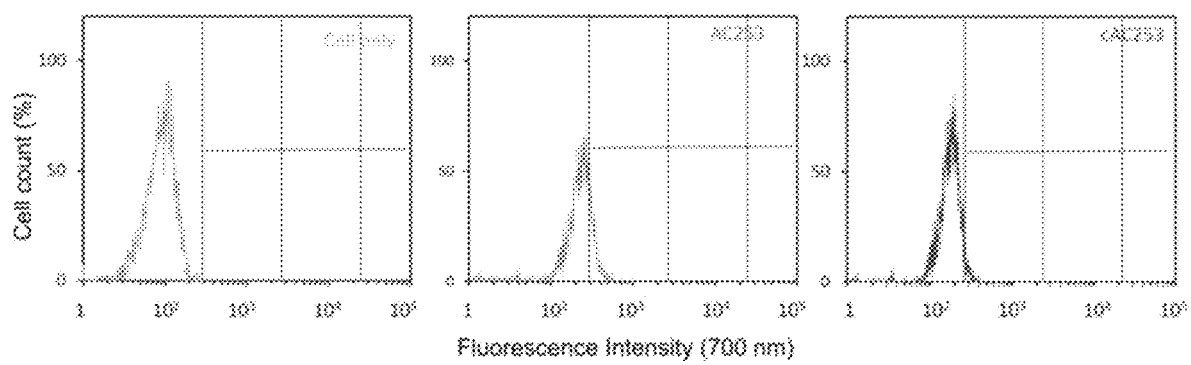
FIG. 7
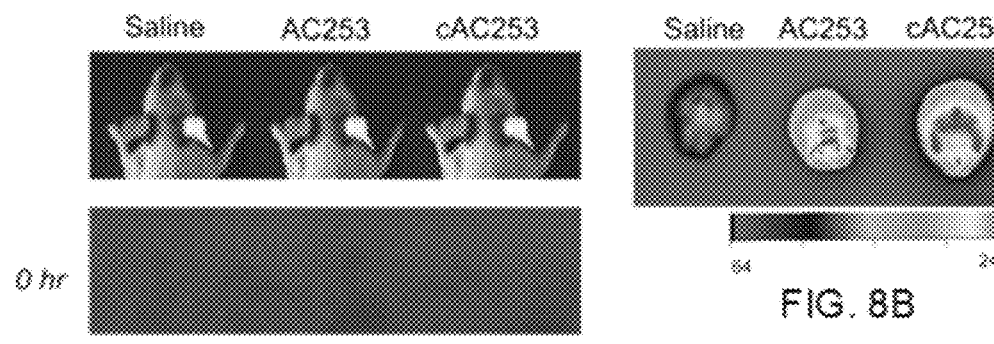
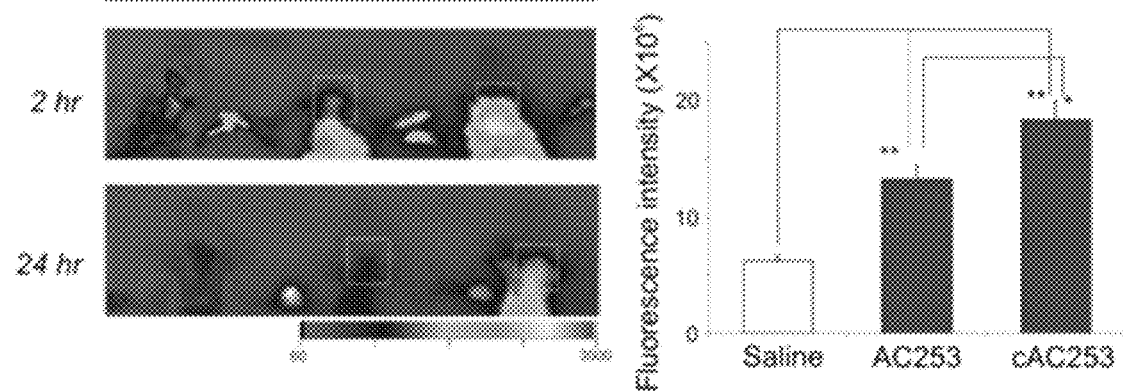
FIG. 8A  FIG. 8C

```
                        SEQUENCE LISTING

<160> NUMBER OF SEQ ID NOS: 17

<210> SEQ ID NO 1
<211> LENGTH: 24
<212> TYPE: PRT
<213> ORGANISM: Artificial Sequence
<220> FEATURE:
<223> OTHER INFORMATION: Amylin receptor antagonist AC253

<400> SEQUENCE: 1

Leu Gly Arg Leu Ser Gln Glu Leu His Arg Leu Gln Thr Tyr Pro Arg
1               5                   10                  15

Thr Asn Thr Gly Ser Asn Thr Tyr
            20

<210> SEQ ID NO 2
<211> LENGTH: 26
<212> TYPE: PRT
<213> ORGANISM: Artificial Sequence
<220> FEATURE:
<223> OTHER INFORMATION: Cyclized AC253

<400> SEQUENCE: 2
```

```
Cys Leu Gly Arg Leu Ser Gln Glu Leu His Arg Leu Gln Thr Tyr Pro
1               5                   10                  15

Arg Thr Asn Thr Gly Ser Asn Thr Tyr Cys
            20                  25
```

<210> SEQ ID NO 3
<211> LENGTH: 12
<212> TYPE: PRT
<213> ORGANISM: Artificial Sequence
<220> FEATURE:
<223> OTHER INFORMATION: R1 - peptide fragment of AC253

<400> SEQUENCE: 3

```
Leu Gly Arg Leu Ser Gln Glu Leu His Arg Leu Gln
1               5                   10
```

<210> SEQ ID NO 4
<211> LENGTH: 12
<212> TYPE: PRT
<213> ORGANISM: Artificial Sequence
<220> FEATURE:
<223> OTHER INFORMATION: R2 - peptide fragment of AC253

<400> SEQUENCE: 4

```
Gly Arg Leu Ser Gln Glu Leu His Arg Leu Gln Thr
1               5                   10
```

<210> SEQ ID NO 5
<211> LENGTH: 12
<212> TYPE: PRT
<213> ORGANISM: Artificial Sequence
<220> FEATURE:
<223> OTHER INFORMATION: R3 - peptide fragment of AC253

<400> SEQUENCE: 5

```
Arg Leu Ser Gln Glu Leu His Arg Leu Gln Thr Tyr
1               5                   10
```

<210> SEQ ID NO 6
<211> LENGTH: 12
<212> TYPE: PRT
<213> ORGANISM: Artificial Sequence
<220> FEATURE:
<223> OTHER INFORMATION: R4 - peptide fragment of AC253

<400> SEQUENCE: 6

```
Leu Ser Gln Glu Leu His Arg Leu Gln Thr Tyr Pro
1               5                   10
```

<210> SEQ ID NO 7
<211> LENGTH: 12
<212> TYPE: PRT
<213> ORGANISM: Artificial Sequence
<220> FEATURE:
<223> OTHER INFORMATION: R5 - peptide fragment of AC253

<400> SEQUENCE: 7

```
Ser Gln Glu Leu His Arg Leu Gln Thr Tyr Pro Arg
1               5                   10
```

<210> SEQ ID NO 8
<211> LENGTH: 12
<212> TYPE: PRT
<213> ORGANISM: Artificial Sequence
<220> FEATURE:
<223> OTHER INFORMATION: R6 - peptide fragment of AC253

-continued

<400> SEQUENCE: 8

Gln Glu Leu His Arg Leu Gln Thr Tyr Pro Arg Thr
1               5                   10

<210> SEQ ID NO 9
<211> LENGTH: 12
<212> TYPE: PRT
<213> ORGANISM: Artificial Sequence
<220> FEATURE:
<223> OTHER INFORMATION: R7 - peptide fragment of AC253

<400> SEQUENCE: 9

Glu Leu His Arg Leu Gln Thr Tyr Pro Arg Thr Asn
1               5                   10

<210> SEQ ID NO 10
<211> LENGTH: 12
<212> TYPE: PRT
<213> ORGANISM: Artificial Sequence
<220> FEATURE:
<223> OTHER INFORMATION: R8 - peptide fragment of AC253

<400> SEQUENCE: 10

Leu His Arg Leu Gln Thr Tyr Pro Arg Thr Asn Thr
1               5                   10

<210> SEQ ID NO 11
<211> LENGTH: 12
<212> TYPE: PRT
<213> ORGANISM: Artificial Sequence
<220> FEATURE:
<223> OTHER INFORMATION: R9 - peptide fragment of AC253

<400> SEQUENCE: 11

His Arg Leu Gln Thr Tyr Pro Arg Thr Asn Thr Gly
1               5                   10

<210> SEQ ID NO 12
<211> LENGTH: 12
<212> TYPE: PRT
<213> ORGANISM: Artificial Sequence
<220> FEATURE:
<223> OTHER INFORMATION: R10 - peptide fragment of AC253

<400> SEQUENCE: 12

Arg Leu Gln Thr Tyr Pro Arg Thr Asn Thr Gly Ser
1               5                   10

<210> SEQ ID NO 13
<211> LENGTH: 12
<212> TYPE: PRT
<213> ORGANISM: Artificial Sequence
<220> FEATURE:
<223> OTHER INFORMATION: R11 - peptide fragment of AC253

<400> SEQUENCE: 13

Leu Gln Thr Tyr Pro Arg Thr Asn Thr Gly Ser Asn
1               5                   10

<210> SEQ ID NO 14
<211> LENGTH: 12
<212> TYPE: PRT
<213> ORGANISM: Artificial Sequence
<220> FEATURE:
<223> OTHER INFORMATION: R12 - peptide fragment of AC253

```
<400> SEQUENCE: 14

Gln Thr Tyr Pro Arg Thr Asn Thr Gly Ser Asn Thr
1               5                   10

<210> SEQ ID NO 15
<211> LENGTH: 12
<212> TYPE: PRT
<213> ORGANISM: Artificial Sequence
<220> FEATURE:
<223> OTHER INFORMATION: R13 - peptide fragment of AC253

<400> SEQUENCE: 15

Thr Tyr Pro Arg Thr Asn Thr Gly Ser Asn Thr Tyr
1               5                   10

<210> SEQ ID NO 16
<211> LENGTH: 14
<212> TYPE: PRT
<213> ORGANISM: Artificial Sequence
<220> FEATURE:
<223> OTHER INFORMATION: R14 - peptide fragment of AC253

<400> SEQUENCE: 16

Leu Gly Arg Leu Ser Gln Glu Leu His Arg Leu Gln Thr Tyr
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Transferrin peptide

<400> SEQUENCE: 17

His Ala Ile Tyr Pro Arg His
1               5
```

BRAIN PENETRANT AMYLIN RECEPTOR BASED PEPTIDES FOR ALZHEIMER'S DISEASE

CROSS REFERENCE TO RELATED APPLICATION

This application claims the benefit of U.S. Provisional Patent Application Ser. No. 62/396,370, filed Sep. 19, 2016, the entirety of which is incorporated herein by reference (where permitted).

FIELD OF THE INVENTION

The present invention relates to amylin receptor antagonists, compositions comprising same, and methods for preparing and using the amylin receptor antagonists and the compositions for treating, preventing, or ameliorating Alzheimer's disease.

BACKGROUND OF THE INVENTION

Alzheimer's disease is the most common form of dementia that is characterized by deposition of amyloid β-protein (Aβ) intra- and extracellularly within cortical and limbic brain structures critical for memory and cognitive functions (Selkoe, 1994 and 2013; Hardy et al., 2002). A central question in Alzheimer's disease research is whether the amyloid protein is a cause or a consequence of the disease. Presently, it appears that the likely answer is both (Hardy, 2009). Evidence strongly supports a role for Aβ in the pathogenesis of Alzheimer's disease, namely: a) Alzheimer's disease associated with inherited Amyloid Precursor Protein (APP) mutations; b) neurotoxicity of soluble oligomeric Aβ when applied to neurons; and c) APP overexpressing mice that recapitulate certain neuropathological and behavioral features of Alzheimer's disease (Liu et al., 2012; Bateman et al., 2012; Patel et al., 2012; Danysz et al., 2012). On the other hand, adverse events in clinical trials for Alzheimer's disease using Aβ vaccine-based therapy, and the subsequent failure of monoclonal antibody therapies and inhibitors of the Aβ generating gamma-secretase enzyme in improving cognitive functions in patients have forced reconsideration of these approaches as disease-modifying treatment strategies in Alzheimer's disease (Liu et al., 2012). Nonetheless, it is hard to imagine a definitive treatment that will not serve to ameliorate in some form the neurotoxic effects of Aβ, since this is a key "upstream" event in Alzheimer's disease pathogenesis (as established by alterations in CSF Aβ levels decades before clinical onset) (Bateman et al., 2012).

Multiple receptors have been implicated in mediating Aβ disruption of neuronal and synaptic processes in Alzheimer's disease, and thus identified as potential targets for developing anti-Aβ therapies (Patel et al., 2012; Danysz et al., 2012). The amylin receptor, comprised of heterodimers of the calcitonin receptor with receptor activity-modifying proteins, serves as a portal for the expression of deleterious effects of Aβ and human amylin (Fu et al., 2012). Amylin is a 37-amino acid peptide hormone that is co-secreted with insulin by beta cells of the pancreas that control glucose levels in blood.

Both Aβ and human amylin are amyloidogenic peptides which share structure-functional relationships; for example, both peptides aggregate and form soluble and insoluble oligomeric intermediates. Amylin has the propensity to aggregate and form amyloid oligomers and fibrils in the pancreas in type 2 diabetes (Westermark et al., 2011) and in Alzheimer's disease brains (Abedini et al., 2013). Aβ and human amylin cause dysfunction and death of neurons preferentially affected in Alzheimer's disease (Jhamandas et al., 2011; 2004). Neurotoxic effects of human amylin and Aβ are expressed through the amylin receptor 3 subtype (AMY3).

Amylin receptor antagonists, such as AC253 (a 24-amino acid peptide), are neuroprotective against Aβ toxicity (Jhamandas et al., 2004; 2011; 2012). Down-regulation of amylin receptor gene expression using siRNA mitigates oligomerized Aβ-induced toxicity (Jhamandas et al., 2011). In Alzheimer's disease transgenic model mice (TgCRND8) which over-express Aβ, amylin receptor was up-regulated within specific brain regions that demonstrate an increased burden of amyloid beta deposits (Jhamandas et al., 2011). Blockade of the amylin receptor with AC253 can reverse impairment of Aβ- or human amylin-induced depression of long-term potentiation, a cellular surrogate of memory, as observed in the hippocampus of Alzheimer's disease mice (TgCRND8) (Kimura et al., 2012). Similar benefits have been reported with pramlintide, a synthetic non-amyloidogenic analog of amylin. While data support a neuroprotective role for this compound, it appears to act as an amylin receptor antagonist rather than an agonist (Kimura et al., 2016). Although amylin receptor antagonist AC253 peptide has therapeutic potential in Alzheimer's disease, it suffers from poor enzymatic stability and an inability to penetrate the blood brain barrier.

SUMMARY OF THE INVENTION

The present invention relates to amylin receptor antagonists, compositions comprising same, and methods for preparing and using the amylin receptor antagonists and compositions for treating, preventing, or ameliorating Alzheimer's disease.

In one aspect, the invention comprises an amylin receptor antagonist comprising cyclic AC253 or a peptide fragment of AC253, wherein the amylin receptor antagonist is capable of binding to an amylin receptor and inhibiting activity of amylin, amyloid-beta protein, or both.

In one embodiment, the amylin receptor antagonist comprises cyclic AC253 having the amino acid sequence of SEQ ID NO: 2, and being brain-penetrant.

In one embodiment, the amylin receptor antagonist comprises a peptide fragment of AC253, wherein the peptide fragment has the amino acid sequence of SEQ ID NO: 3, 4, 5, 6, 7, 8, 9, 10, 11, 12, 13, 14, 15, or 16, and is brain penetrant.

In one embodiment, the peptide fragment has the amino acid sequence of SEQ ID NO: 7, and is capable of binding to AMY1 and AMY3 receptors.

In one embodiment, the peptide fragment has the amino acid sequence of SEQ ID NO: 12, and is capable of binding to AMY1 receptor.

In one embodiment, the peptide fragment has the amino acid sequence of SEQ ID NO: 16, and is capable of binding to AMY1 and AMY3 receptors.

In another aspect, the invention comprises a composition or pharmaceutical composition comprising the above amylin receptor antagonist, and a pharmaceutically acceptable carrier.

In another aspect, the invention comprises a method of treating, preventing, or ameliorating a disease in a subject, comprising administering to the subject an effective amount of AC253, or the above amylin receptor antagonist or a composition comprising same. In one embodiment, the disease is Alzheimer's disease.

In one embodiment, the disease is treated, prevented or ameliorated with chronic administration of the amylin receptor antagonist. In one embodiment, chronic administration comprises administration of the amylin receptor antagonist at least once a week, at least once a day, or at least twice a day for a period of at least one month.

In one embodiment, the disease is treated, prevented or ameliorated by chronic intracerebroventricular infusion of the amylin receptor antagonist. In one embodiment, chronic intracerebroventricular infusion is conducted for at least five months. In one embodiment, the amylin receptor antagonist comprises AC253.

In another aspect, the invention comprises use of an effective amount of AC253 or the above amylin receptor antagonist for treating, preventing, or ameliorating a disease in a subject. In one embodiment, the disease is Alzheimer's disease.

In yet another aspect, the invention comprises a method for inhibiting activity of amylin, amyloid-beta protein, or both in a cell or organism, comprising exposing the cell or the organism to the above amylin receptor antagonist. In one embodiment, the cell comprises a neuronal cell.

Additional aspects and advantages of the present invention will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described by way of an exemplary embodiment with reference to the accompanying simplified, diagrammatic, not-to-scale drawings. In the drawings:

FIGS. 2A-G show the effects of chronic intracerebroventricular infusions of amylin receptor antagonist, AC253, on behavioral performance and spatial memory in a TgCRND8 AD mouse model.

FIGS. 3A-F show the effects of AC253 on Aβ, expression levels of neuron, synapses-associated proteins, microglia and amylin receptor in mice brains.

FIGS. 6A-D show flow cytometry histograms, graphs, and fluorescence microscopy images.

FIG. 7 shows flow cytometry histograms.

FIGS. 8A-D show results of in vivo NIRF brain imaging, ex vivo images of brains, quantification of brain fluorescence intensity, and brain sections from ex vivo experiments.

DETAILED DESCRIPTION OF PREFERRED EMBODIMENTS

Before the present invention is described in further detail, it is to be understood that the invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a", "an", and "the" include plural referents unless the context clearly dictates otherwise.

The present invention relates to amylin receptor antagonists, compositions comprising same, and methods for preparing and using the amylin receptor antagonists and compositions for treating, preventing, or ameliorating Alzheimer's disease.

As used herein, the term "amylin" refers to a 37 amino acid peptide hormone which is co-secreted with insulin from the pancreatic β-cell.

As used herein, the term "amyloid-beta protein" refers to peptides of 36-43 amino acids resulting from cleavage of the amyloid precursor protein, and which form the main component of neurotoxic amyloid plaques found in the brains of Alzheimer patients.

Figure 1:
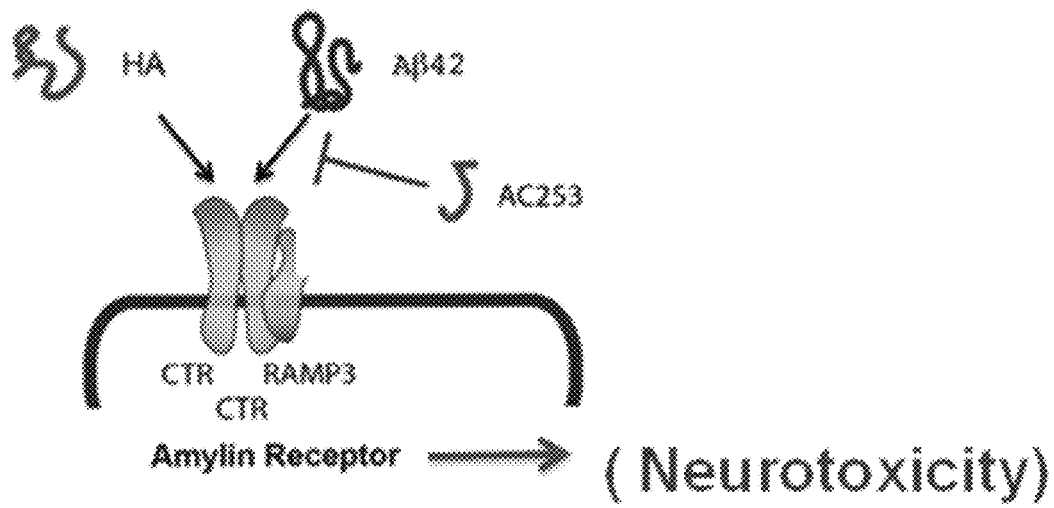
FIG. 1 is a schematic prior art diagram (Jhamandas et al., 2004).

As used herein, the term "amylin receptor" refers to a receptor complex which binds amylin and amyloid-beta protein. The amylin receptor consists of the calcitonin receptor (CTR) dimerized with one of three known subtypes of receptor activity-modifying protein (RAMP1, RAMP2, RAMP3). FIG. 1 is a schematic prior art diagram showing the interactions of human amylin (HA), amyloid-beta (Aβ42), and amylin receptor antagonist peptide (AC253) with the amylin receptor (AMY3) formed of calcitonin receptors (CTR) and the receptor activity-modifying protein (RAMP3) and functional consequence (neurotoxicity) of the interactions of either human amylin (HA) or amyloid-beta (Aβ42) (Jhamandas et al., 2004). Both amylin (HA) and amyloid-beta protein (Aβ42) bind and directly activate the amylin receptor and trigger biological and neurotoxic effects.

As used herein, the term "amylin receptor antagonist" refers to a compound useful as an antagonist of the amylin receptor, or which binds to, but does not activate, the amylin receptor. The amylin receptor antagonist displaces and blocks the binding of amylin or amyloid-beta protein to the amylin receptor, thereby inhibiting the activity of amylin or amyloid-beta protein.

In one embodiment, the amylin receptor antagonist comprises AC253. The literature on amylin antagonism reports the use of "AC253." The "AC" prefix indicates the compound's identity within the peptide library of Amylin Pharmaceuticals Inc. As used herein, the term "AC253" refers to a peptide having the amino acid sequence of SEQ ID NO: 1 (Ac-LGRLSQELHRLQTYPRTNTGSNTY) and which is capable of binding to the amylin receptor, thereby inhibiting the activity of amylin, amyloid-beta protein, or both.

In the development of the present invention, it was found that chronic administration of AC253 may improve spatial memory and learning in a murine model. AC253 may also increase synaptic integrity, and reduce microglial activation without discernible side effects. In one embodiment, the present invention comprises a method of treating, preventing, or ameliorating Alzheimer's disease by chronic administration to a subject of a therapeutically effective amount of AC253. As used herein, the term "chronic administration" refers to repeated administration of AC253 to the subject. In such treatment, AC253 can be administered as least once a week, more typically at least once a day, and even possibly at least twice or three times a day for a period of at least one month. In one embodiment, AC253 is chronically administered for at least five months.

Peptide based drugs have limited therapeutic utility for central nervous system disorders due to their limited blood brain barrier permeability (Vassar, 2014). AC253 is extremely hydrophilic in nature, and the linear form of AC253 is not brain penetrant. As used herein, the term "brain penetrant" means being capable of crossing the blood brain barrier. The effects of AC253 on spatial memory in vivo were initially assessed through an intracerebroventricular route of administration as previously described. While beneficial, chronic intracerebroventricular administration of AC253 may be impractical.

Therefore, a modified peptide of AC253 was prepared and tested to improve its physicochemical and biological activity and brain penetrability compared to its linear counterpart. In one embodiment, the modified peptide comprises cyclized AC253. As used herein, the term "cyclized AC253" (abbreviated as "cAC253") refers to a form of AC253 in which one amino acid has become linked to another to form a closed ring. In one embodiment, cAC253 has two cysteine amino acids at the C- and N-termini in contrast to AC253, and is cyclized using a disulfide linkage. In one embodiment, cAC253 comprises the amino acid sequence of SEQ ID NO: 2 (C-LGRLSQELHRLQTYPRTNTGSNTY-C). In one embodiment, the invention comprises processes for preparing cAC253. Exemplary processes for preparation are described in the Examples.

Without being bound by any theory, gaining a fixed geometry through cyclization may enhance peptide specific and efficient binding to the amylin receptor. Since amylin receptors exist as several subtypes (AMY1, AMY2, AMY3), the fixed geometry of cAC253, in comparison to linear AC253, may enhance its selectivity for particular receptor subtypes (AMY1, AMY3) that are more prevalent in the brain (Husmann et al., 2000; Hay et al., 2006). In addition, cyclization may enhance peptide enzymatic stability (Di, 2014).

It was confirmed that cAC253 is superior to linear AC253 with respect to multiple properties. cAC253 is proteolytically stable, brain penetrant, and binds to hippocampal amylin receptors while retaining its neuroprotectant properties. In one embodiment, cAC253 is capable of binding to AMY3 receptor, thereby inhibiting the activity of amylin. As used herein, the term "AMY3 receptor" refers to a heterodimeric complex of the calcitonin receptor and RAMP3.

As a further development of the present invention, peptide fragments of AC253 were isolated which retain the beneficial effects of the parent compound AC253, but offer advantages in terms of their synthesis, stability, and administration (Table 1). These shorter amylin receptor antagonist peptides based upon the AC253 sequence were found to be proteolytically stable and brain penetrant when administered systemically. Their affinity for the amylin receptor and efficacy in vitro and in vivo were assessed. In one embodiment, the present invention comprises processes for preparing peptide fragments of AC253. Exemplary processes for preparation are described in the Examples.

TABLE 1

Peptide Fragments of AC253

| Peptide Fragment of AC253 | Amino Acid Sequence | Sequence Identification Number |
|---|---|---|
| R1 | LGRLSQELHRLQ | SEQ ID NO: 3 |
| R2 | GRLSQELHRLQT | SEQ ID NO: 4 |
| R3 | RLSQELHRLQTY | SEQ ID NO: 5 |
| R4 | LSQELHRLQTYP | SEQ ID NO: 6 |
| R5 | SQELHRLQTYPR | SEQ ID NO: 7 |
| R6 | QELHRLQTYPRT | SEQ ID NO: 8 |
| R7 | ELHRLQTYPRTN | SEQ ID NO: 9 |
| R8 | LHRLQTYPRTNT | SEQ ID NO: 10 |

TABLE 1-continued

Peptide Fragments of AC253

| Peptide Fragment of AC253 | Amino Acid Sequence | Sequence Identification Number |
|---|---|---|
| R9 | HRLQTYPRTNTG | SEQ ID NO: 11 |
| R10 | RLQTYPRTNTGS | SEQ ID NO: 12 |
| R11 | LQTYPRTNTGSN | SEQ ID NO: 13 |
| R12 | QTYPRTNTGSNT | SEQ ID NO: 14 |
| R13 | TYPRTNTGSNTY | SEQ ID NO: 15 |
| R14 | LGRLSQELHRLQTY | SEQ ID NO: 16 |

In one embodiment, the amylin receptor antagonist comprises a peptide fragment of AC253. In one embodiment, the peptide fragment comprises the amino acid sequence of SEQ ID NO: 3, 4, 5, 6, 7, 8, 9, 10, 11, 12, 13, 14, 15, or 16. In one embodiment, the peptide fragment of AC253 is capable of binding to the amylin receptor, thereby inhibiting the activity of amylin, amyloid-beta protein, or both.

In one embodiment, the peptide fragment comprises the amino acid sequence of SEQ ID NO: 7 (i.e., the peptide fragment of AC253 designated as "R5"), and is capable of binding to AMY1 and AMY3 receptors, thereby inhibiting the activity of amylin. As used herein, the "AMY1 receptor" refers to a heterodimeric complex of the calcitonin receptor and RAMP1. As used herein, the "AMY3 receptor" refers to a heterodimeric complex of the calcitonin receptor and RAMP3. R5 is capable of reversing the effects of amylin and amyloid-beta protein; thus, R5 may serve as a disease-modifying therapeutic.

In one embodiment, the peptide fragment comprises the amino acid sequence of SEQ ID NO: 12 (i.e., the peptide fragment of AC253 designated as "R10"), and is capable of binding to AMY1 receptor, thereby inhibiting the activity of amylin.

In one embodiment, the peptide fragment comprises the amino acid sequence of SEQ ID NO: 16 (i.e., the peptide fragment of AC253 designated as "R14"), and is capable of binding to AMY1 and AMY3 receptors, thereby inhibiting the activity of amylin.

AC253, cAC253, and R1-R14 of the present invention may be formulated for therapeutic use. In one embodiment, the invention comprises a composition or a pharmaceutical composition comprising one or more of AC253, cAC253, and R1-R14 as an active ingredient(s) in combination with one or more pharmaceutically acceptable carriers. As used herein, the term "carrier" means a suitable vehicle which is biocompatible and pharmaceutically acceptable, including for instance, liquid diluents which are suitable for administration. As used herein, the term "biocompatible" means generating no significant undesirable host response for the intended utility. Most preferably, biocompatible materials are non-toxic for the intended utility. Thus, for human utility, biocompatible is most preferably non-toxic and otherwise non-damaging to humans or human tissues. As used herein, the term "pharmaceutically acceptable" means a substance which does not significantly interfere with the effectiveness of AC253, cAC253, and R1-R14, and which has an acceptable toxic profile for the host to which it is administered.

In one embodiment, the invention comprises a composition or pharmaceutical composition comprising one or more of AC253, cAC253, and R1-R14, and a pharmaceutically acceptable carrier.

Suitably, pharmaceutical compositions comprising one or more of AC253, cAC253, and R1-R14 may in various embodiments be formulated for administration parenterally in dosage unit formulations containing conventional non-toxic pharmaceutically acceptable carriers, adjuvants and vehicles. The term "parenteral" as used herein includes subcutaneous injections, intradermal, intra-articular, intra-cerebroventricular, intravenous, intramuscular, intravascular, intrasternal, intrathecal injection or infusion techniques.

The pharmaceutical compositions may be in the form of a sterile injectable aqueous suspension. This suspension may be formulated according to known art using those suitable dispersing or wetting agents and suspending agents. The sterile injectable preparation may also be a sterile injectable solution or a suspension in a non-toxic parentally acceptable diluent or solvent. Among the acceptable vehicles and solvents that may be employed are water, Ringer's solution and isotonic sodium chloride solution. In addition, sterile, fixed oils may be employed as a solvent or suspending medium. Adjuvants such as local anaesthetics, preservatives and buffering agents may optionally also be included in the injectable solution or suspension.

Useful dosages of one or more of AC253, cAC253, and R1-R14 depend upon many factors that are well known to those skilled in the art, for example, the type and pharmacodynamics characteristics of the adenoviral vector; age, weight and general health condition of the subject; nature and extent of symptoms; any concurrent therapeutic treatments; frequency of treatment and the effect desired.

Certain embodiments of the invention thus relate to methods and uses of AC253, cAC253, and R1-R14 as amylin receptor antagonists which bind to, but do not activate, the amylin receptor. AC253, cAC253, and R1-R14 may be used to displace and block the binding of amylin or amyloid-beta protein to the amylin receptor, thereby inhibiting the activity of amylin or amyloid-beta protein. The amylin receptor antagonist may be used to reduce incidence of, reduce, treat, diminish, or prevent a disease or disorder in a subject where it is of benefit to reduce amylin or amyloid-beta protein activity. In one embodiment, the disease is Alzheimer's disease. Therapeutic uses of AC253, cAC253, and R1-R14 in diseases or disorders, methods of prevention or treatment using AC253, cAC253, and R1-R14, and uses of AC253, cAC253, and R1-R14 to prepare medicaments for therapeutic use are also contemplated in certain embodiments of the invention. Certain embodiments relate to the therapeutic use of AC253, cAC253, and R1-R14 in humans.

In one embodiment, the invention provides a method of treating, preventing, or ameliorating a disease or disorder in a subject, comprising administering to the subject an effective amount of one or more of AC253, cAC253, and R1-R14 or a composition comprising same. As used herein, the term "disease" includes, but is not limited to, Alzheimer's disease. As used herein, the term "subject" means a human or other vertebrate. As used herein, the term "effective amount" means any amount of a formulation of AC253, cAC253, and R1-R14 useful for treating, preventing, or ameliorating a disease or disorder upon administration. An effective amount of the composition provides either subjective relief of symptoms or an objectively identifiable improvement as noted by the clinician or other qualified observer. As used herein, the terms "treating," "preventing" and "ameliorating" refer to interventions performed with the intention of alleviating the symptoms associated with, preventing the development of, or altering the pathology of a disease, disorder or condition. Thus, in various embodiments, the terms may include the prevention (prophylaxis), moderation, reduction, or curing of a disease, disorder or condition at various stages. In various embodiments, therefore, those in need of therapy/treatment may include those already having the disease, disorder or condition and/or those prone to, or at risk of developing, the disease, disorder or condition and/or those in whom the disease, disorder or condition is to be prevented.

Embodiments of the present invention are described in the following Examples, which are set forth to aid in the understanding of the invention, and should not be construed to limit in any way the scope of the invention as defined in the claims which follow thereafter.

Example 1—Materials

All chemicals were analytical grade and used without further purification. hAmylin, and $A\beta_{1-42}$ were from rPeptide (Bogart, Ga.). Rink amide resin (0.4 mmol/g), (2-(6-chloro-1H-benzotriazole-1-yl)-1,1,3,3-tetramethylaminium-hexafluoro phosphate) (HCTU), 1-hydroxybenzotriazole (HOBt), and the Fmoc-amino acids were from NovaBiochem (San Diego, Calif.). Fmoc-amino acids were supplied with the following side-chain protection: Fmoc-Asn(Trt)-OH, Fmoc-Arg(Pbf)-OH, Fmoc-Cys(Trt)-OH, Fmoc-Gln(Trt)-OH, Fmoc-His(Trt)-OH, Fmoc-Ser(OtBu)-OH, Fmoc-Thr(OtBu)-OH, Fmoc-Tyr(OtBu)-OH. Trifluoroacetic acid (TFA), N,N-Diisopropylethylamine (iPrNEt), piperidine, and triisopropylsilane (iPr3SiH) were from Sigma-Aldrich (Canada). Human serum was from Aldrich (Canada). Cyanine5.5 NHS ester dye was from Lumiprobe (USA). Amino-PEG500 cellulose membrane derivatized with a polyethylene (PEG) was from (Intavis AG, Germany). N,N'-Diisopropylcarbodiimide (DIC), N,Ndimethylformamide (DMF), 1-Ethyl-3-(3-dimethylaminopropyl)-carbodiimide) (EDC), N-hydroxysuccinimide (NHS), N-methyl morpholine (NMM), trifluoroacetic acid (TFA), dimethyl sulfoxide (DMSO), piperidine and all other reagents were from Sigma-Aldrich (USA). Soluble oligomeric Aβ1-42 were from rPeptide (Bogart, Ga.) and h-Amylin, human calcitonin, rAmy, and $sCT_{8-32}$ were from American Peptide (Sunnyvale, Calif.). AC187 was from Bachem. Pramlintide was from Amylin Pharmaceuticals. Taking the peptide content into account, these peptides were dissolved in water to produce 1 mM solutions (calculated, not directly measured). hAmy was from American Peptide, or made in-house as previously described (Chisti et al., 2005). hAmy was dissolved in dimethyl sulfoxide to produce a 1 mM solution. Hexafluoro-2-propanol pretreated $A\beta_{1-42}$ was from rPeptide, and was solubilized in 1% $NH_4OH$ to produce a 500 µM solution and sonicated for 1 minute to dissolve. All peptides were stored as aliquots in microcentrifuge tubes at −30° C., and freeze-thaw cycles were limited, except for $A\beta_{1-42}$, which was stored in single use aliquots at −80° C.

Example 2—Animal Models and Drug Administration

Age-matched, wild-type littermate (C57BL/6 background) male or female mice were used. TgCRND8 mice (human APP695 transgene array incorporating Swedish K670M/N671L and Indiana V717F mutations superimposed upon a C57BL6 genetic background) which exhibit Aβ plaques and cognitive defects by 6 months of age (Chishti et al., 2001) were obtained from Dr. David Westaway (University of Alberta). Heterozygous CTR (het CTR) mice (C57BL/6J background) with a 50% deletion of CTR were obtained from Drs. R. A. Davey and J. D. Zajac (Department of Medicine, Austin Health, University of Melbourne, Heidelberg, Victoria, Australia). Mice were housed individually under standard laboratory conditions (12/12-h light/dark cycle, lights on at 0600 h) with a room temperature of 21° C. Water and food were available ad libitum unless otherwise indicated. All tests were performed during the light phase between 0900 and 1600 h in accordance with institutional guidelines. The mice were 3 months old at the onset of testing.

A microcannula was stereotaxically inserted into the right cerebral ventricle (0.12 right lateral and 0.06 posterior to bregma, 3 mm deep) of isoflurane-anesthetized mice, and connected to an osmotic pump (Alzet; model 2004) implanted subcutaneously on the back of the mouse. The pump infused a solution of either aCSF or AC253 in aCSF into the ventricle at a rate of 0.25 L/h to yield an estimated concentration of 1 µM AC253 in the mouse CSF at equilibrium based upon the known CSF dynamics in the mouse brain (Di Pardo et al., 2012). The pump reservoir was replaced every 28 days for a total of 5-6 months. Animals were monitored on a daily basis for signs of treatment-related toxicity, such as poor grooming, lethargy, loss of bodyweight, and abnormal behavior. After completion of medication and behavioral tests, all mice were killed with an overdose of isoflurane anesthetic, perfused transcardially with saline, and the brains were harvested. The left hemisphere per animal was frozen for biochemical analysis (Western blot, ELISA), and the right hemisphere retained for histological analysis.

Example 3—Behavioral Testing i) Morris Water Maze (MWM)

The MWM apparatus consisted of a 2 m circular blue plastic pool filled with water (24-25° C.), which was rendered opaque by the addition of non-toxic white paint. An escape platform (20 cm in diameter) was submerged 0.5 cm under the water level. Dark posters differing in shape (one per wall) provided distant landmarks. The behavior of a mouse was recorded by a video camera connected to a video tracking system (HVS Image 2100, HVS Image, Buckingham, UK).

The pool was surrounded by a white curtain, and a mouse was released facing the wall at points (N, E, S, W) which were chosen semi-randomly. The mice were trained for 7 days (7 trials per day) to find a submerged platform located in the centre of the NE quadrant of the pool (target quadrant, TQ). The trial ended when a mouse found and climbed onto the platform within 120 seconds. If the mouse failed to find the platform, it was guided to the platform by an experimenter. After a 10 second post-trial time on the platform, the mouse was placed in a holding cage to dry. Mice were tested with inter-trial interval of about 50 minutes. Memory was evaluated in probe trial, administered on day 8 as the first trial of the day. During probe trial, the platform was removed from the pool. Memory for the platform location was expressed as the percent of time spent in TQ.

ii) T-Maze Alternation

One week prior to the start of the experiment, the mice were placed on a food restricted diet and gradually reduced to 85-90% of their free-feeding weights. One day before the start of the experiment, the mice were familiarized with the choc-cereal reward in their home cage. Pre-training began with 2 days of habituation to the maze. Food reward was scattered down each of the arms and in the food well, and the mice were allowed to explore the maze for 5 minutes.

Training on the forced-choice alternation rule began the following day. The mice received 5-8 trials per daily session for 10 days. During the forced sample run, one of the side arms of the maze was blocked. After the mouse turned into the preselected arm, it was allowed to eat food reward that had been previously placed in the food well. The mouse was then picked up from the maze and immediately returned to the start arm. The next trial was a choice trial. The mouse was allowed to run up the stem of the maze and was now given a free choice between the left and the right turn arms. The mouse received food reward only if it turned in the direction opposite to that in the forced trial run (i.e., non-matching). The choice of the sample arm (left or right) was randomly assigned with the only stipulation that no arm could be selected as the sample on more than two consecutive trials. The % correct alternations were obtained.

Example 4—Western Blot

Frozen brain tissues were homogenized in cold RIPA buffer with protease inhibitors and proteins were isolated and measured using BCA assay (BioRad, Mississauga, ON, Canada). Proteins were loaded at 50 μg per lane on a 12% polyacrylamide gel for CTR, RAMP3, NeuN, synapsin1, phospho-synapsin, and Iba1, or 4-20% polyacrylamide gradient gel (BioRad) for APP. Proteins were transferred to nitrocellulose membrane, and blocked with LiCOR blocking buffer. Blots were incubated with primary antibodies overnight at 4° C. on a shaker. Primary antibody used for CTR (1:1000 rabbit; Thermo Scientific), RAMP3 (1:1000 rabbit; Santa Cruz Biotechnology), 6E10 for APP (1:5000 mouse; 6E10; Covance), NeuN (1:1000, rabbit, Abcam), synapsin-1 (1:1000 rabbit, Abcam), synaptophysin (1:1000, rabbit, Abcam), phosphosynapsin (1:1000, rabbit, Abcam), Iba1 (1:1000, rabbit, Wako), β-tubulin (1:1000, rabbit, Cell Signaling Technology, Inc.) and β-actin (1:10000 mouse, Sigma-Aldrich). IRDye 800CW goat anti-rabbit and IRDye 680CW goat anti-mouse were used as secondary antibodies. Blots were imaged using LiCor Odyssey image system.

Example 5—ELISA for $A\beta_{1-42}$ Measurement

Soluble $A\beta_{1-42}$ were quantified in frozen hemispheres using colorimetric ELISA kits following the protocol provided (Thermofisher scientific, ON, Canada). In brief, hemi-brains were homogenized on ice for 3 hours in 0.1 M Tris/5M guanidine buffer with protease inhibitor (1 ml volume for each brain). The homogenized brain was centrifuged at 21,000 g for 20 minutes at 4° C. The supernatant was collected and diluted with PBS buffer pH 7.4 (1:100) prior its plate loading. Standard curves were plotted using human $A\beta_{1-42}$ standards provided in the ELISA kit. All samples were analyzed in duplicate. The plate was measured at 450 nm and the intensity of color was directly proportional to the amount of $A\beta_{1-42}$ in the tissue and data expressed as ng/mg wet tissue.

Example 6—Immunofluorescent-Histological Staining

For immunostaining, 20 am thick brain sections were cut using a Cryostat (Leica CM1850), fixed with 4% paraformaldehyde in PBS, permeabilized using 0.3% Triton X-100 and stained with Aβ (6E10), Iba1, and CTR antibody, followed by fluorescent secondary antibody (goat anti mouse Alexa Fluor-546 and donkey anti rabbit Alexa Fluor-488) and mounted in DAPI mounting media. Fluorescent microscopy images were acquired with an Axioplan-2 fluorescence microscope with AxioVision software (Carl Zeiss Ltd., Toronto, ON, Canada). Amyloid plaque size and area were analyzed with Image J.

Example 7—Peptide Synthesis and Fluorescence Labeling

Peptides (AC253, cAC253, T7 transferin specific) were synthesized on a 0.1 mmol scale rink amide resin preloaded with tyrosine or cysteine using the Fmoc/tBu strategy by an automated synthesizer (Tribute, Protein Technology Inc., USA). First 10 amino acids couplings were performed as single coupling cycles, followed by double coupling for further amino acids. The Fmoc group was removed using 20% piperidine in DMF (3 min×2). Resin cleavage and removal of the amino acid side-chain protecting groups was undertaken by incubating the resin in cleavage cocktail of TFA/iPr$_3$SiH/H$_2$O (v/v/v; 95/2.5/2.5) for 2 hours at room temperature. The crude peptides were precipitated and triturated with cold diethyl ether, isolated (centrifugation), dissolved in 20% MeCN (aq) containing 0.1% TFA and lyophilized. To cyclize the cAC253 peptide via the flanking D-cysteines, the crude peptide (61.2 mg) was dissolved in 0.1 mM Tris buffer pH 8.3 having 20% of DMSO to accelerate disulfide bond formation, and the mixture was stirred at room temperature in an open flask for 48 h. All peptides were purified on RP-HPLC using semi-preparative C18 (Vydac) column with gradient of 10-50% acetonitrile/water mixture for 45 min with flow rate of 1.5 ml/min, then 50-100% in 10 min then back to 10% in 5 min. The peak containing the peptide was collected and lyophilized, retention times observed were 31.5 min, 29 min, and 24 min for AC253, cAC253, and transferin peptides respectively. Peptides were characterized using MALDI-TOF mass spectrometry.

To validate peptide library results and investigate peptides amylin receptor binding and antagonistic activity, selected peptides were synthesized, fragments R5, and R14 were the most promising AMY3 binding sequences, while fragments R11, and r13 were selected as negative controls. Davalintide peptide was also synthesized as mentioned. Peptide fragments, Davalintide and AC253 were synthesized on rink Amide MBHA resin at 0.1 mmol scale, using Fmoc/tBu strategy by an automated synthesizer (Tribute, Protein Technology Inc., USA). Fmoc chemistry, employing four equivalent of Fmoc protected amino acids and coupling agents like NMM and HCTU. The Fmoc group was removed as described above. All peptides were then purified on RP-HPLC using semi-preparative C18 (Vydac) column using gradient of 15-55% acetonitrile for 55 min with flow rate of 2 ml/min. Water used in HPLC contained 0.05% TFA. Approximately 95-97% purity was gained for purified peptides, which was assessed using Vydac analytical C18 HPLC column. The peak containing the peptide was collected and lyophilized, retention times observed were 18.5 min, 19.2 min, 18.1 and 18.3 min for R5, R14, R11 and R13 peptides respectively. Molecular mass of each peptide was evaluated by MALDI-TOF mass spectrometry. Calcd. For R5, [M+H]$^+$ 1527.5; found [M+H]$^+$ 1526.5; Calcd. for R14, [M+H]+ 1713.1.6; found [M+H]+ 1712.1; Calcd. for R11, [M+H]+ 1351.6; found [M+H]+ 1351.8 and Calcd. for R13, [M+H]+ 1375.6; found [M+H]+ 1375.8.

For peptides fluorescent labeling, an extra β-alanine was added to the N-terminus of the peptide as a spacer. Subsequent labeling of AC253, cAC253, and AC253 peptides with the near-infrared fluorescent dye Cy5.5-NHS ester (molecular weight 750.42D, ex 673 nm, and em 707 nm) through the N-terminal amino group acylation was carried out as follows. Peptides (2 mM) were dissolved in 0.5 mL of DMSO and 20 μL of Cy5.5 NHS ester dye was added (1.4 mg, 2 mM) with 30 μl triethylamine and rotated on the shaker in the dark for 4 hours at room temperature, then at 4° C. overnight. The labeled peptides were purified from unincorporated dye using RP-HPLC using gradient of 30-70% acetonitrile for 45 minutes with flow rate of 1.5 ml/min then 70-100 in 10 minutes, then back to 30% in 5 minutes.

Retention times were 35 minutes, 34.5 minutes, and 33 minutes for AC253, cAC253, and T7 transferin targeting peptides, respectively. The labeling efficiency/molar ratio was one Cy5.5 molecule per each peptide. Retention times were 35 min, 34.5 min, 33 min and 35 min for R5, R14, R11 and R13 fragments respectively.

HPLC purified peptides were pooled and lyophilized to yield the fluorescent labeled peptides as blue powder in >97% purity as assessed using Vydac analytical C18 RP-HPLC column. Stock solution of peptides (1 mM) were prepared in 100% DMSO, 100 μl aliquots were stored at −80° C., and before using DMSO was removed by lypholization and the peptides were dissolved in the required buffers.

Example 8—Lipophilicity

Peptides hydrophobicity was determined using the shake flask method and 1-octanol/water partition coefficient (log Po/w) was determined. Peptides AC253, or cAC253 (1 mg) was dissolved in 1 ml PBS buffer, then 1 ml 1-octanol was added and the vials were shaken vigorously for 30 minutes, followed by centrifuged for 10 minutes at 5000 g to separate the two layers. Peptide concentration (area) in both phases (1-octanol and water) were analyzed by RP-HPLC. The final log Po/w value was calculated by dividing the concentration (C) of the peptide in the two phases as presented by the area under the peak (partition coefficients=$C_{1-octanol}/C_{water}$).

Example 9—Cell Culture and Relevant Assays a) To investigate peptides amylin receptor affinity, GFP-positive HEK293 cells that stably expressed AMY3 receptor (AMY3-293) as previously reported (Fu et al., 2012) were used. For control, GFP-positive HEK293 wild type cells were used. HEK293 cells were cultured in DMEM (Invitrogen) with 10% FBS (Invitrogen) and grown at 37° C., 5% C02. For cAMP measurements, AMY3-293 cells were plated on 24-well plates overnight. Cells were stimulated for 30 minutes with hAmylin over a concentration range (1 pM-10 μM). Cellular cAMP levels were measured using a parameter cyclic AMP assay kit (R&D Systems) according to the manufacturer's instructions. For in-cell Western blot cAMP quantification, mouse monoclonal anti-cAMP (R&D Systems) was used as a primary antibody, and IRDye 800 goat anti mouse antibody (LI-COR) was used as a secondary antibody. Plates were imaged using an Odyssey Infrared Imaging System (LI-COR), and the integrated intensity was normalized to the total cell number on the same well. Data was plotted, and non-linear regression was fitted with four parameters using Prism software (GraphPad Software, La Jolla, Calif.).

b) To investigate the antagonistic activity of peptides against Aβ cytotoxicity in vitro, HFNs and N2a cells were used. Cells were seeded to 5000 cells/well in a 96-well plate in MEM-10% FBS and DMEM/OptiMEM-5% FBS for overnight. Cells in culture media were preincubated for 8 hours with or without AC253 or cAC253, and followed by treatment with $A\beta_{1-42}$ for 24 hours. At the end of treatment, 20 μl of 5 mg/ml methylthiazolyldiphenyl-tetrazolium bromide (MTT) was added to each well, and incubated at 37° C. for 3 hours. Medium was removed, 100 μl of MTT solvent (isopropanol with 4 mM HCl) added to each well, and the plates were incubated for 30 minutes at room temperature on a rotating shaker. Plates were analyzed on a microplate reader at a 562-nm wavelength. The Live/Dead assay kit was purchased from Invitrogen and assay followed the production instruction. The assayed cells were fixed with 4% paraformaldehyde in PBS and photo imaged with Axio Zeiss fluorescent microscopy. The dead cells were further counted using ImageJ software.

c) For fluorescence peptide uptake, AMY3-293 cells were grown on coverslips in 12 well plates at a density of $1.5 \times 10^5$ cells/well overnight at to 50% confluence and incubated with Cy 5 peptides (5 μM) diluted in culture medium at 37° C. for 1 hour. Cells were washed three times with PBS, fixed in 4% paraformaldehyde in PBS for 10 minutes, and mounted in DAPI mounting media. The cells were imaged using a Zeiss Axioplan-2 microscope (Carl Zeiss Microscope Systems, Toronto, ON, Canada) using AxioVision software (version 4.8) with identical photo settings.

d) For flow cytometry studies, AMY3-293 cells were used to determine cell binding and uptake and binding of Cy5-AC253, and Cy5-cAC253 peptides. Cell were plated at a density of $1.5 \times 10^5$ cells/well and cultured overnight in 12-well plates at 37° C. Cy5 labelled peptides (5 μM) were added and incubated for 1 hour at 37° C. in serum free media. The culture media was discarded, and cell monolayers were washed with PBS containing 2 mM EDTA and 0.5% BSA adjusted to pH 7.4 at 37° C. Cells were washed again with cold buffer and incubated with 0.25% trypsin to remove cell surface-associated fluorophores. Cells were dispersed in FACS solution (10% FBS in PBS) and analyzed using a FACSCanto II flow cytometer (BD Biosciences, USA) selecting a detection window between 720 and 840 nm. Fluorescence histograms and dot plots were generated using the data were processed with FLOWJO software (Tree Star, Inc, USA). At least 10,000 gated events per sample were analyzed. The experiment was repeated with different peptide concentration ranging from 0.5-10 μM, and mean fluorescence intensity of peptides was extrapolated. To further study the cell uptake mechanism, cells were preincubated with cytochalasin D (cytoD, 20 g/ml) for 30 minutes, and the experiment was repeated as above. To determine the energy dependent mechanism, cell uptake experiment was undertaken at 4° C., and for the competition experiment, cells was pre-incubated with amylin (30 μM) for 30 minutes, and the experiment was repeated.

e) For cAMP measurements, AMY3-293 cells were plated on 24-well plates overnight. Cells were then incubated with peptide fragments R5, R14 at a concentration of 1 μM for 30 min. Then cells were stimulated for 30 min with hAmylin, over a concentration range (1 pM-10 μM). Cellular cAMP levels were measured using a parameter cyclic AMP assay kit (R&D Systems) according to the manufacturer's instructions. Data were plotted, and non-linear regression was fitted with four parameters using Prism software (GraphPad Software, La Jolla, Calif.).

f) To investigate the antagonistic activity of peptide fragments against Aβ cytotoxicity in vitro, (human fetal neurons) HFNs, human neuroblastoma, SK-N-SH cells and N2a mouse neuroblastoma cells were used. Cells were seeded to 5000 cells/well in a 96-well plate in MEM-10% FBS and DMEM/OptiMEM-5% FBS for overnight. Cells in culture media were preincubated for 8 h with or without AC253 or fragments R5, R14, R11, and followed by treatment with Aβ$_{1-42}$ for 24 h. At the end of treatment, 20 μl of 5 mg/ml methylthiazolyldiphenyl-tetrazolium bromide (MTT) was added to each well, and incubated at 37° C. for 3 h. Medium was removed, 100 μl of MTT solvent (isopropanol with 4 mM HCl) added to each well, and the plates were incubated for 30 min at room temperature on a rotating shaker. Plates were analyzed on a microplate reader at a 562-nm wavelength.

Example 10—In Vivo and Ex Vivo NIRF (Near Infrared Fluorescence) Imaging

For in vivo imaging experiments, 6-12 month-old TgCRND8, age-matched wild-type littermate, and heterozygous CTR knockdown mice (50% CTR expression level compared to wild type control mice and presumably with 50% AMY receptor expression level) were used (n=5 in each group). The animals were anesthetized with ketamine ip injection. The fur was shaved from the head and dorsal side of the body to avoid laser scattering caused by hair. The mice were injected ip with Cy5-labeled AC253 or cAC253 (0.1 mmol in 200 μl saline), then placed on an imaging platform (dorsal side facing down) and scanned at different timepoints 0, 0.5, 1, 2, 4, 24 hours. Wild type mice injected with 200 μl saline were used as a background.

Images were acquired with a Kodak IS2000MM Image station (GE Healthcare Systems/ART Inc.), excitation filter 625/20 band pass, emission filter 700 W band pass, light source was 150 W quartz halogen lamp set to 100 (max). Images were captured with a CCD camera set to F stop=0, FOV=150, FP=0. Exposure time was 2 min per image for NIRF image and 1 s for visible image. To evaluate for fluorescence concentration, the region of interest was drawn around the brain region and analyzed using the Kodak ID 3.6 software and the mean fluorescence intensity was recorded.

Additionally, a competition in vivo experiment was also carried out. Mice were injected ip with 40 μg of Cy5.5 labeled cAC253, along with 5× (200 μg) of unlabeled cAC253 peptide. Brains were then extracted and scanned ex-vivo for fluorescence concentration. For ex vivo histological study, brains were excised and embedded in OCT, then sliced into 20-μm slices, co-stained with DAPI in mounting medium. Fluorescence images were observed with Axio Zeiss fluorescent microscopy.

For ex vivo imaging experiments and peptide brain uptake, age matched 6-month-old wild-type littermate (C57BL/6 background) mice were used. Mice were injected ip with peptides (R5, R14, AC253) at 0.2 nmoles of peptides in single dose in 200 μl normal saline. After 2 hours the mice were then sacrificed to collect their brains, and imaged using the Kodak imager as described above, but with an exposure time of 3 min per image for NIRF image.

To evaluate for fluorescence concentration, a region of interest was drawn around the brain region and analyzed using the Kodak ID 3.6 software and the mean fluorescence intensity was recorded. For ex vivo histological studies, brains were excised, embedded in OCT, then sliced into 20-μm slices, co-stained with DAPI in mounting medium. Florescence images were observed with Axio Zeiss fluorescent microscopy.

For peptide R5 brain uptake in comparison to Davalintide, wild-type littermate (C57BL/6 background) mice and heterozygous CTR knockdown mice (50% CTR expression level compared to wild type control mice and presumably with 50% AMY receptor expression level) were used (n=5 in each group). Mice were injected with a single dose and then sacrificed, and the brains were extracted after 2 hours from injection. Fluorescence in brains was quantified as previously described.

Example 11—Detection of cAC253 in Brain Using LCMS/MS

Brains were collected from three mice that received Cy5-cAC253 peptide (0.1 mmol, 400 μg/each) and mechanically homogenized in ice cold homogenizing buffer using a polytron (0.1 M Tris-HCl, pH 5.0; 50 mM sucrose; 10× protease inhibitor cocktail). Cold ACN (100% with 0.05% formic acid) was added to brain homogenates to reach a final 65% ACN concentration, and then they were further homogenized. The mixture was stirred on a rotating mixer for 10 minutes in a cold room and centrifuged (5,500 g for 15 minutes at 4° C.). The supernatants were collected, frozen at −80° C., and vacuum-dried in a lyophilizer. Dehydrated samples were reconstituted in mobile phase (65:35 ACN/water with 0.05% TFA). The reconstituted samples were injected onto the LC MS/MS. For detecting Cy5-cAC253 peptide concentration in the brain, the fluorescence in the brain homogenate was imaged in a 96-well plate compared to a 4 point concentration curve of cAC253 standard in control brain homogenate.

Example 12—Human Serum and Mice Liver Homogenate Peptide Stability

The stability and the degradation profile of the cAC253 in human serum and mice liver homogenate was assessed and compared to AC253 peptide. For the serum stability experiments, human serum or liver homogenate (250 μL) were added to DMEM medium (650 μL) in a 1.5 mL Eppendorf tube to mimic a biological system. The temperature was equilibrated at 37±1° C. for 30 minutes before adding 100 μL of the peptide stock solution (1 mM solution in 10% DMSO in sterile water). An aliquot of reaction solution (100 μL) was removed from the sample at different time points 0, 3, 5, 10, 20, and 30 minutes added to pure methanol (300 μL) for precipitation of the serum proteins present in the human serum proteins by centrifugation (10,000 rpm, 5 minutes). The clear supernatant was analyzed by reversed phase HPLC, and the appropriate fractions were collected for identification using MALDI-TOF. Proteolysis kinetics of the peptides was analyzed by following the decrease in the concentration of the intact peptide as a function of time. The $t_{1/2}$ half-lives of peptides were calculated.

Example 13—In Vivo Pharmacokinetics and Bio-Distribution Studies

The rate of entry and clearance of cAC253 from the brain has been investigated. Mice were treated with cAC253 at 0, 0.2, 2, and 20 mg/kg/day in single dose in 200 μl normal saline. There were 3 mice in each dose group. After 2 hours the mice were sacrificed to collect their brains which were imaged in a Kodak imager. For time based studies, mice were injected with 20 mg/kg cAC253 peptide, then sacrificed (three per time point) at 0, 0.5, 2, 6, 24 and 48 hours after dosing. The heart, liver, lung, spleen, intestine, stomach, kidney and brain were excised after perfusion with PBS, and kept in dry ice before Kodak imaging. Fluorescence was quantified, and analyzed as previously.

Example 14—Peptide Library Screening

A peptide array library derived from AC253 peptide sequence comprising 14 short peptide sequences namely, R1-R14 (R-R13 are 12 amino acids, peptide R14 is 14 aa), was synthesized in duplicate on a cellulose membrane using SPOT synthesis. Briefly, peptide fragments were designed by selecting the first 12 amino acids from N-terminus, skipping one amino acid and moving towards C-terminus to yield 13 sequences R1-R13, and peptide R14 is the first 14 amino acid of the N-terminus region of AC253. The peptide array was synthesized on a PEG-500-derivatized cellulose membrane with a free amino terminal group using a semi-automatic robot AutoSpot ASP222 (Intavis AG, Germany). Synthesis of peptides on PEG500 derivatised cellulose membrane was started by attaching first β-alanine residue (linker) to the cellulose membrane and subsequently peptides synthesized from the C-terminus. Fmoc protected amino acids (0.25 mM/mL) activated with HOBt and DIC were spotted on the membrane in 60 nL aliquots per spot by a robotic syringe, yielding a peptide loading of 0.4 μmol/cm$^2$. After coupling of the Fmoc amino acid, the membrane was removed from the platform of robotic system and treated with acetic anhydride (2%) to cap any free remaining amino groups. Deprotection of Fmoc of coupled amino acid was conducted using 20% piperidine in DMF. After deprotection, membrane was washed with DMF and IPA, air-dried and carefully repositioned on the robotic system to repeat the coupling cycles in order to complete the peptide sequence. At the end, all peptides were N-terminally acetylated. The final removal of side chain protecting groups was performed by treating the membrane with a cocktail of reagents, comprised of TFA (15 mL), DCM (15 mL), tri-isopropylsilane (0.9 mL), and water (0.6 mL), for about 3 h. After extensive washing with DCM, DMF, and ethanol, the membrane was dried with cold air and stored in a sealed bag at −20° C. until use.

Example 15—Peptide Array-Cell Binding Assay

To screen the peptide library for amylin receptor binding affinity, transfected GFP-positive Human Embryonic Kidney 293 cells that express AMY3 receptor (CTR+RAMP3) was used. For controls, wild type GFP-positive HEK293 cells and HEK293 cells that express calcitonin receptor (CTR) cells were used. HEK293 cells were cultured with DMEM (Invitrogen) with 10% FBS (Invitrogen) and grown at 37° C., 5% $CO_2$. The peptide array membrane was incubated with 20 ml GFP-cells (75,000/ml) in serum free media for 3 hr, and after washing, the net fluorescence intensity of each peptide spot due to bound cells was quantified using a Kodak imager. Each cell-binding experiment was repeated twice for same cell line. Duplicate peptide spots, two scans, and two different experiments were used to calculate net fluorescence intensity. Membrane was regenerated after each cell-binding experiment for further use. For membrane regeneration, the bound cells were removed by first washing with ethanol for 5 min, followed by treatment with 0.1 N HCl for 20 min. The peptide array membrane was then washed with DMF (4×20 min), ethanol (3×3 min), and finally dried in air.

Example 16—Slice Preparation and Electrophysiology

Brains were quickly removed from mice following decapitation, placed in a cold artificial cerebral spinal fluid (aCSF) on a vibratome chamber, and transverse sections cut through the hippocampus. The aCSF contained (in millimolar 124 NaCl, 3 KCl, 2.4 $CaCl_2$, 2 $MgCl_2$, 1.25 $NaH_2PO_4$, 26 $NaHCO3$, and 10 D-glucose and was equilibrated with 95% $O_2$ and 5% $CO_2$. Hippocampal slices (400-μm thick) were maintained in aCSF-filled holding chamber at room temperature for at least 1 h and individually transferred to the submerged glass bottom recording chamber, which was constantly perfused with aCSF (2 ml/min) at 30° C. Field excitatory postsynaptic potential (fEPSP) was recorded with a metallic (Pt/Ir) electrode (FHC, Bowdoin, Me.) from the stratum radiatum layer of Cornu ammonis 1 region of the hippocampus (CA1) area, and the Schaffer collateral afferents were stimulated with 100-μs test pulses via a bipolar cluster electrode (FHC). For long-term potentiation (LTP) experiments, the stimulus strength was set to elicit 40-50% of the maximum fEPSP amplitude and test pulses were delivered to Schaffer collaterals once every 30 s. LTP was induced by 3-theta-burst stimulation (3-TBS) protocol (each burst consisted of four pulses at 100 Hz with a 200-ms interburst interval). Before 3-TBS or drug application, the responses were monitored for at least 10 min to ensure a stable baseline of fEPSP. To determine whether the magnitude of LTP differed significantly between groups, average responses during the last 20-min block of recordings (40-60 min after TBS) were compared.

Example 17—Drugs and Application

Soluble oligomeric $A\beta_{1-42}$, Fragments R5, R10, R11 and h-Amylin were used. $A\beta_{1-42}$ was purchased from rPeptide, and h-Amylin were purchased from American Peptide. All drugs and chemicals were applied directly to the slice via bath perfusion, which allowed for a complete exchange of the perfusate in less than a minute and a half.

Example 18—Statistical Analysis

The statistical data are presented as mean±S.E.M unless otherwise specified. Significance was determined one-way analysis of variance (ANOVA), followed by Tukey's post hoc test with Prism software (GraphPad Prism 5, GraphPad Software, San Diego, Calif.). Differences between groups were considered to be significant at $P<0.05$.

Example 19—Results

Discussed below are results obtained by the inventors in connection with the experiments of Examples 1-18.

i) Chronic AC253 Treatment Improves Cognitive Deficits in a Transgenic Animal Model of Alzheimer's Disease.

TgCRND8 mice carry combined APP Swedish (K670M/N671L) and Indiana (V717F) mutations, resulting in an aggressive neuropathology evident by 6 months when the animals also exhibit diffuse and plaque amyloid deposits (Chishti et al., 2001; Janus et al., 2000). These mice exhibit normal behavior at 3-4 months of age, but by 6 months show a progressive deterioration of cognitive function and spatial memory with increased AP burden.

FIGS. 2A-G show the effects of chronic intracerebroventricular (icv) infusions of amylin receptor antagonist, AC253, on behavioral performance and spatial memory in a TgCRND8 AD mouse model. (FIG. 2A) Schedule and timeline for behavioral testing and administration of icy AC253. (FIGS. 2B-C) Data from Morris Water Maze (MWM) testing shows daily escape latencies during platform trials of either wild-type (Wt) or TgCRND8 (Tg) mice receiving icy artificial CSF (CSF) or AC253 at 3 and 8 months of age (n=7-8 mice in each group; ***p<0.001 TgCSF vs. TgAC253). (FIGS. 2D-E) Probe trials (to test for retention of platform placement) show comparative analysis of time spent in the four quadrants between treatment groups of Wt and TgCRND8 mice. Target Q, quadrant where the platform is located. (FIGS. 2F-G) Graph showing the percentage of alteration in T-maze test. (n=6-7 mice in each group, *p<0.05, **p<0.01).

Figure 2A:
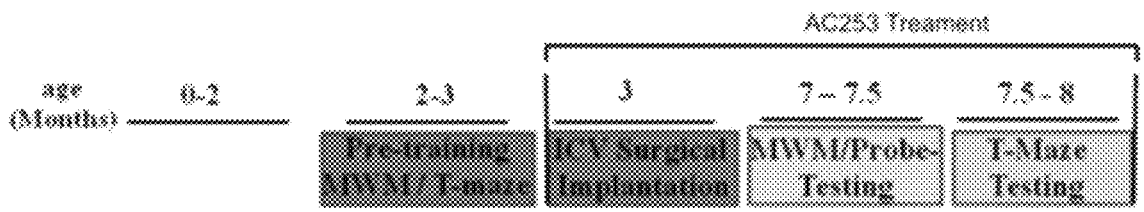
Figures 2B, 2C:
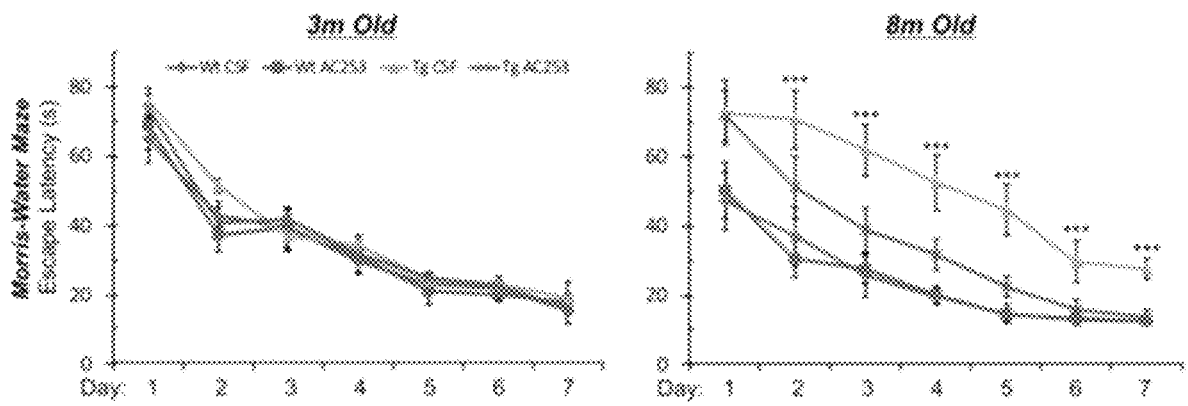

To determine whether amylin receptor antagonists can prevent spatial memory and learning, chronic intracerebroventricular (icy) infusions of AC253 or CSF were performed in TgCRND8 or wild-type (Wt) littermate control mice starting at 3 months of age (prior to the development of amyloid pathology), and behaviour was serially measured every two months using MWM and T-maze tests up to 8 months (FIG. 2A). At 3 months of age, no differences were detected in either the MWM or T-maze between Wt and Tg mice (FIGS. 2B, 2D, 2F). However, at 8 months of age (after 5 months of treatment), the TgCRND8 mice receiving AC253 showed a marked improvement in latencies to locate the hidden platform over their littermates receiving CSF. Wt controls showed no memory deficits with either AC253 of CSF infusions (FIG. 2C). TgCRND8 mice that were treated with AC253 showed enhanced and persistent memory in probe trials for location of the target quadrant (FIG. 2E). For the T-maze, TgCRND8 mice that received AC253 correctly identified the food arm of the maze compared to other groups (FIG. 2F-G). These results indicate that AC253 may prevent cognitive decline in aged APP expressing mice.

In spite of the duration of drug infusions, none of the mice receiving AC253 showed any signs of off-target effects (e.g., sedation, visible signs of motor dysfunction, abnormal feeding or drinking behaviour and weight loss, changes in gross appearance such as hair loss, lack of grooming) or changes in body weight. Mortality within the groups of TgCRND8 mice receiving either CSF or AC253 was identical at 20%, a figure consistent with that reported by other groups that have used this genetic strain of mice (Chishti et al., 2001; Janus et al., 2000). The long term central administration of amylin receptor antagonist, AC253, therefore appears to be a viable, relatively safe disease-modifying treatment in an AD mouse model.

It has been previously shown using several in vitro experimental paradigms that the deleterious effects of Aβ are expressed via amylin receptors and that blockade of these receptors with antagonists, such as AC253 or pramlintide, ameliorates Aβ toxicity and restores LTP, a cellular surrogate of memory (Jhamandas et al., 2011; Kimura et al., 2016). The inventors surmised that the same mechanism, i.e. blocking the brain amylin receptors, could account for the in vivo improvement in spatial memory and learning observed in AC253-treated TgCRND8 AD mice. The brains of Wt and TgCRND8 mice receiving CSF or AC253 were examined to determine whether the antagonism of amylin receptors with AC253 affected markers of AD pathology.

FIGS. 3A-F show the effects of AC253 on Aβ (APP processing, Aβ plaques, Aβ soluble oligomers), expression levels of neuron (NeuN), synapses-associated proteins (synaptophysin, synapsin 1, and phosphosynapsin), microglia (Iba1) and amylin receptor (CTR and RAMP3) in TgCRND8 mice brains after 5 months of icy injection. (FIGS. 3A-B) Western blots and quantitative analysis of APP in TgCRND8 mice brain homogenates receiving either AC253 or CSF as control. (n=5 for each group, mean+SEM, student t test.). (FIG. 3C) ELISA of $Aβ_{1-42}$ quantification in brain homogenates. (n=5 for each group, mean±SEM, student t test) (FIG. 3D) 6E10 immunohistochemical Aβ plaques staining in TgCRND8 mice brain homogenates receiving either AC253 or CSF as control. (Scale bar, 200 m.) (FIG. 3E) Representative western blot images and quantitative analysis in brain homogenates of AC253 treatment group compared to CSF treatment group. (n=5 for each group, mean+SEM, student t test. *p<0.05, **p<0.01). (FIG. 3F) Iba1 immunostaining in TgCRND8 mice brain homogenates receiving either AC253 or CSF as control. (Scale bar, 200 m.)

Figure 3D:
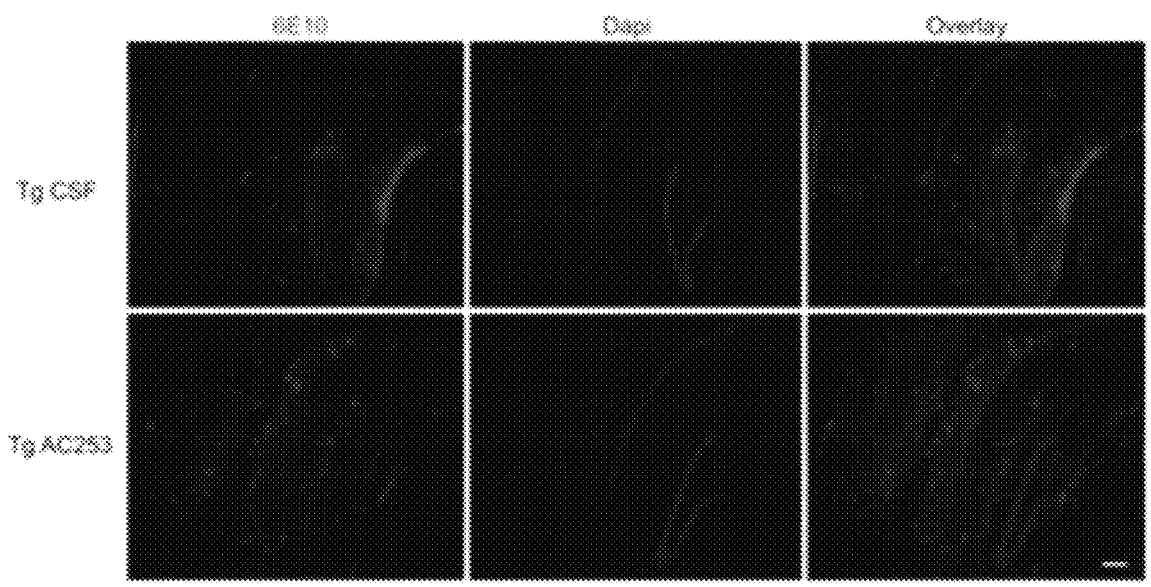

There were no significant difference in the levels of soluble $Aβ_{1-42}$ or APP expression between the two Tg groups as measured by ELISA, and Western blot respectively (FIG. 3A-B). Aβ deposition also did not reveal significant difference in either the number of Aβ plaques, or total area of Aβ-positive profiles in AC253 treated Tg group compared to Tg CSF mice (FIG. 3C). Therefore it is unlikely that AC253 exerts its beneficial effects on spatial memory and learning by reducing the amyloid burden as has been reported for systemically administered pramlintide (Zhu et al., 2015). The amylin receptor (CTR, RAMP3 proteins) expression levels in the brain showed no noticeable difference in the levels of either protein between brains of the two transgenic groups receiving either AC253 or CSF (FIG. 3D).

Figure 3E:
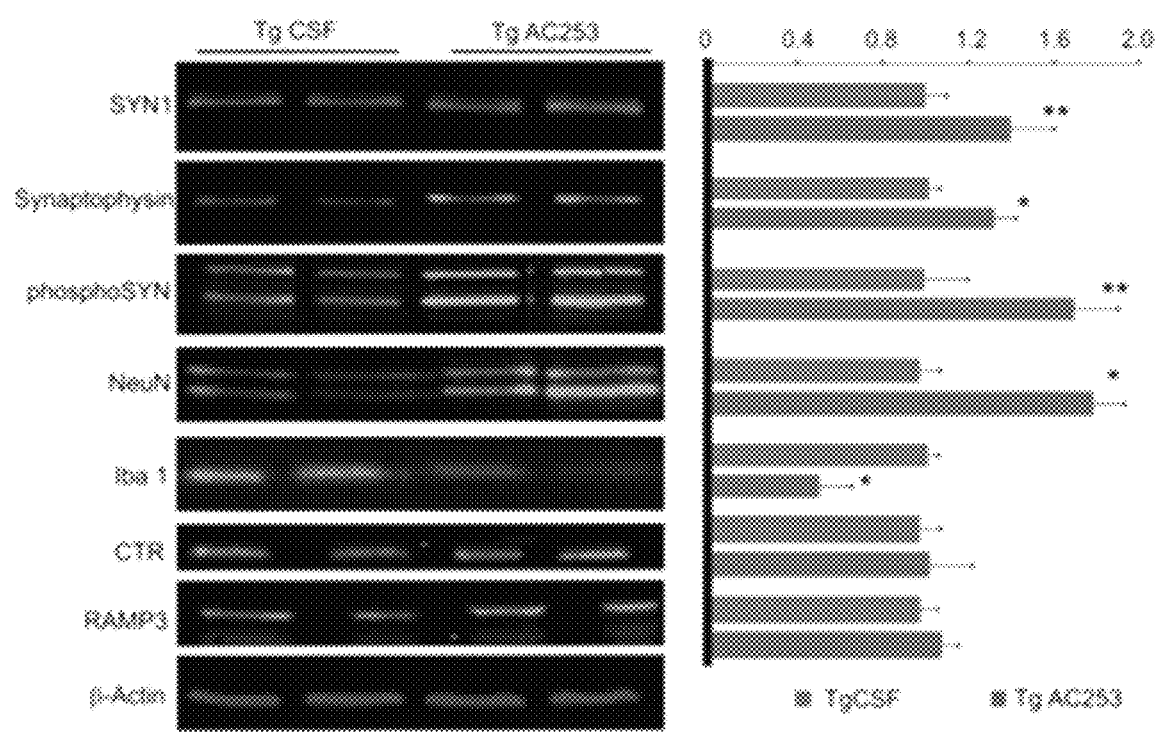
Figure 3F:
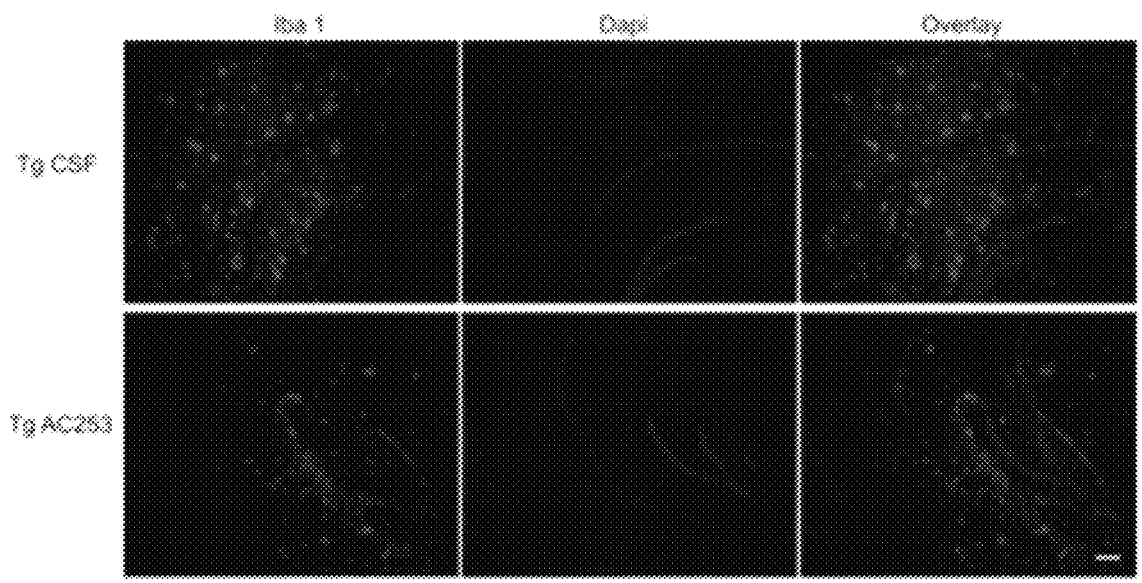

Tg AC253 treated group showed an increase of 40% and 30% in the expression level of synaptic proteins, synapsin 1 and synaptophysin, respectively, compared with Tg CSF controls (FIG. 3D). The expression levels of Iba-1, a microglial marker, was significantly reduced (by 50%) in Tg-AC253 group compared to Tg-CSF. This finding was further confirmed using immunofluorescence staining (FIG. 3E). AC253 may thus improve not only synaptic function as has been observed for in vitro studies of LTP (Kimura et al., 2012, 2016), but also attenuate disruption of synaptic integrity in TgCRND8 mice that is attributed to increased Aβ burden. Amylin receptors have also been reported on human microglia and deemed to participate in Aβ-induced activation of inflammasome and cytokine release (Jhamandas et al., 2015). Thus, attenuation of this AP-driven inflammatory cascade by blockade of amylin receptors with AC253 could explain the decreased microglial activation in brains of TgCRND8 mice.

ii) Cyclic AC253 Blocks AMY3 Receptor Activation and Aβ Neuronal Cell Death In Vitro.

Figure 4A:
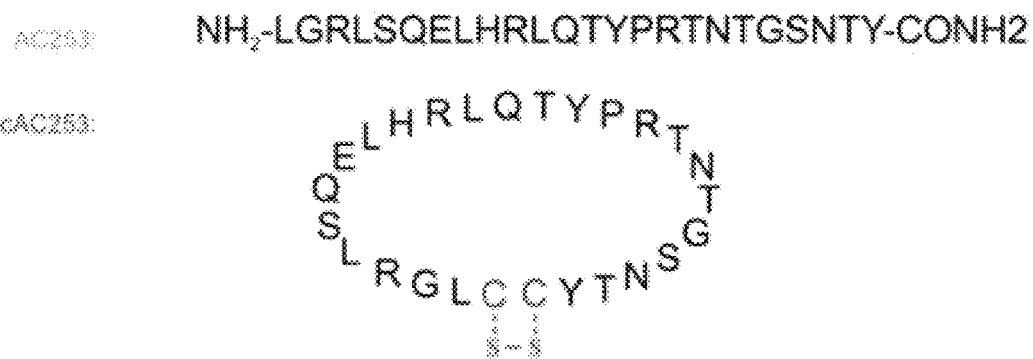
FIGS. 4A-F show results indicating that cAC253 retains its amylin receptor antagonist and neuroprotective properties against $A\beta_{1-42}$ cytotoxicity. The sequences in FIG. 4A from top to bottom are set forth in SEQ ID Nos: 1 and 2.
Figure 4B:
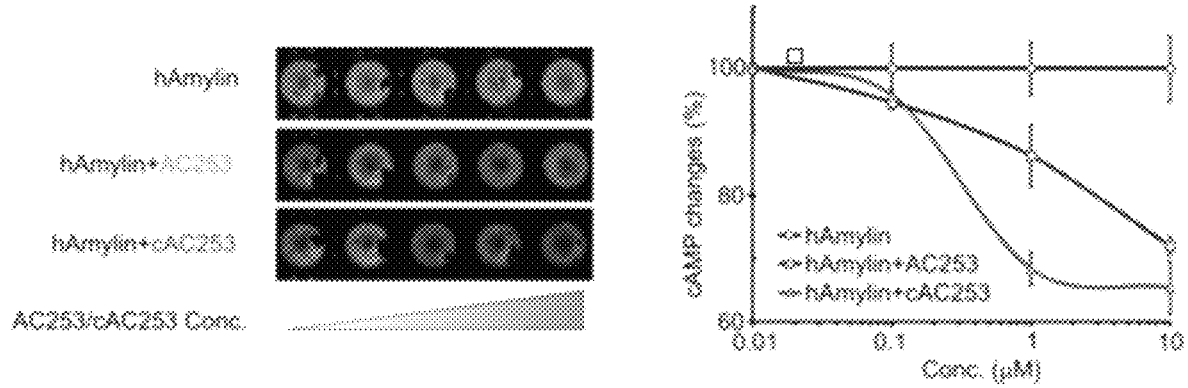
Figure 4C:
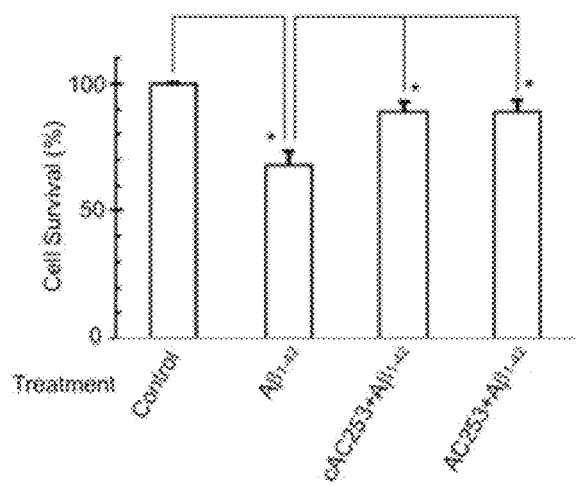
Figure 4D:
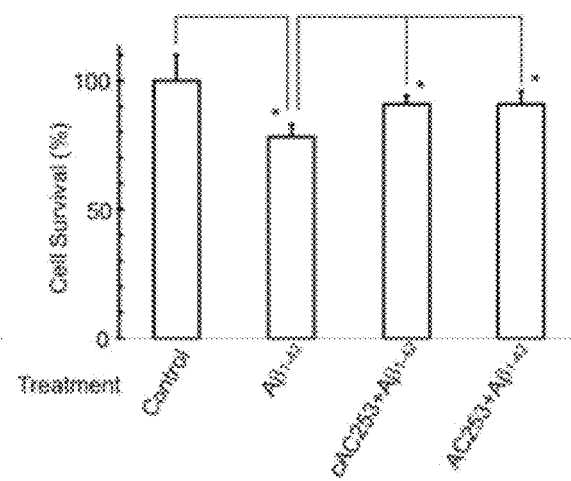
Figure 4E:
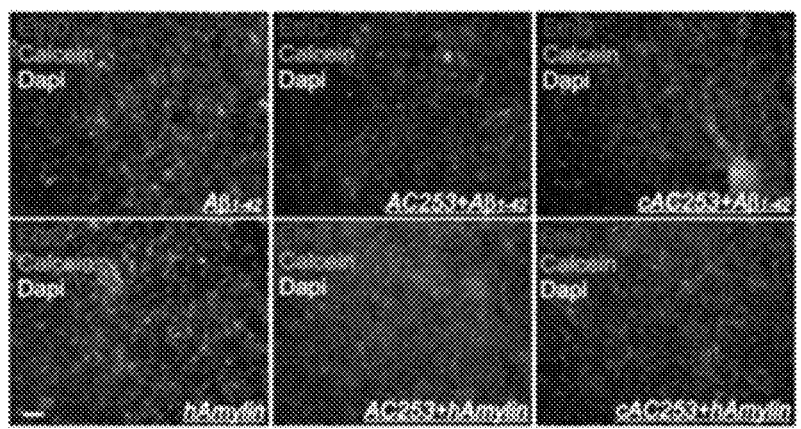
Figure 4F:
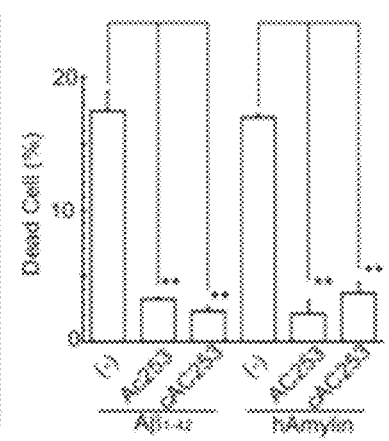
Figures 5A, 5B:
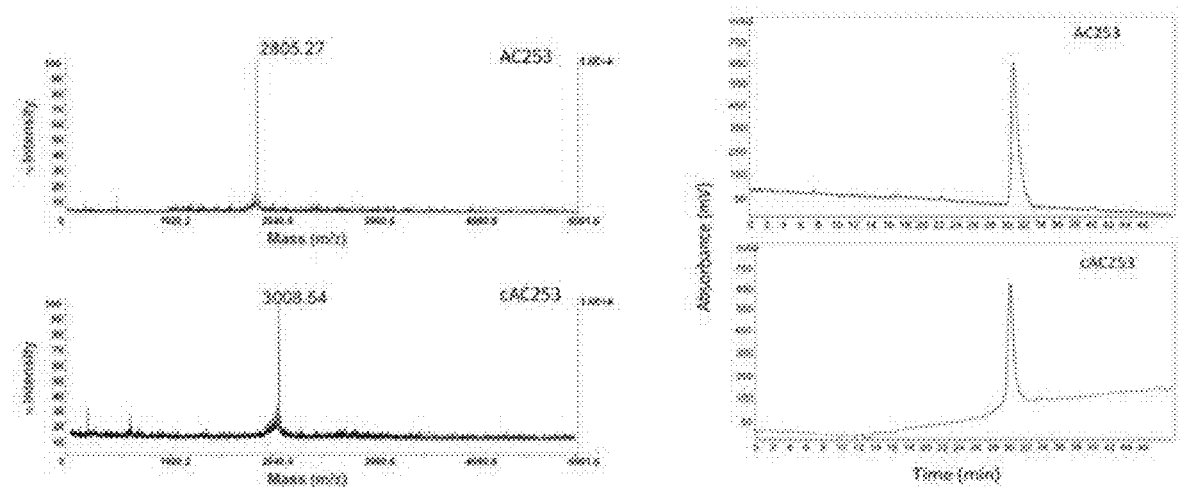
FIGS. 5A-D show results from MALDI-TOF and analytical RP-HPLC chromatograms.
Figure 5C:
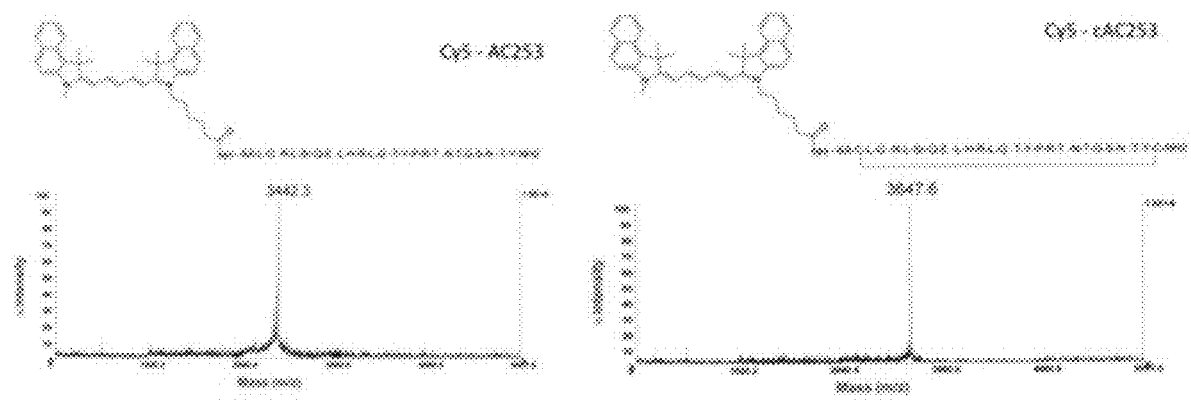
Figure 5D:
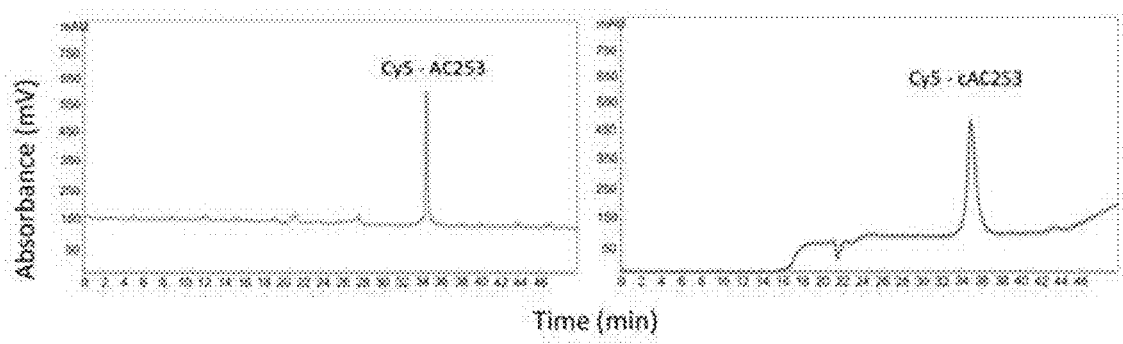

FIGS. 4A-F show results indicating that cAC253 retains its amylin receptor antagonist and neuroprotective properties against $Aβ_{1-42}$ cytotoxicity. (FIG. 4A) AC253 and cAC253 amino acid sequences and structure. cAC253 has two additional cysteine amino acids at the C-, and N-termini compared to AC253, and is cyclized using disulfide linkage. (FIG. 4B) In-cell Western assay showing both AC253 and cAC253 are capable of inhibiting hAmylin effects on the cellular levels of cyclic adenosine-monophosphate (cAMP) via AMY3 receptor activation in HEK293 AMY3-expressing cells. Graph showing changes in cAMP levels in AMY3 expressing HEK293 cells after exposure to different concentrations of AC253 and cAC253 peptides in presence of 1 μM hAmylin. (FIGS. 4C-D). $Aβ_{1-42}$ (10 μM) applied to primary cultures of human fetal neurons (HFNs) or N2a neuronal cell line induces cell death (measured by MTT assay) that can be attenuated by pre-applications of 10 μM either AC253 or cAC253) (FIG. 4E) Photomicrographs of live (calcein-green fluorescence)/dead (ethidium-red fluorescence) assay in HFNs, showing the effect of cAC253 or AC253 pre-incubation on the $Aβ_{1-42}$ and hAmylin induced cell death. (Scale bar=100 μm.) (FIG. 4F) Histograms showing quantification of live/dead assay. (n=8, *p<0.05; **p<0.01).

A conformational constraint was imposed on the AC253 structure by placing two cysteine residues at both the C, and N-termini, and cyclizing it through disulfide bond formation (FIG. 4A). Synthetic peptides AC253 and cAC253 were obtained in high yields, 40% and 55%, respectively, and purity greater than 97% for both peptides (TABLE 2).

to pramlintide (Symlin®), cAC253 offers multiple advantages including better solubility at physiological pH (Wang et al., 2014), superior brain penetrability when administered

TABLE 2

Characterization data of AC253, cAC253, and transferrin peptides, MALDI-TOF mass Spectrometry, partition coefficient, yield and purity

| Peptide | Sequence | [M + H]+ Cal. | [M + H]+ Obs. | Partition coefficient | Yield (%) | Purity (%) |
|---|---|---|---|---|---|---|
| AC253 | LGRLSQELHRLQTYPRTYPRTNTGSNTY-(NH2) (SEQ ID NO: 1) | 2805.3 | 2805.2 | 1.05 | 55 | 98.6 |
| cAC253 | CLGRLSQELHRLQTYPRTYPRTNTGSNTYC-(NH2) (SEQ ID NO: 2) | 3007.9 | 3008.5 | 1.22 | 40 | 97.5 |
| Transferrin peptide | HAIYPRH-(NH2) (SEQ ID NO: 17) | 893.5 | 893.4 | NA | 70 | 98 |

FIGS. 5A-D show the following results: (FIG. 5A) MALDI-TOF of pure peptides AC253, cAC253 peptide showing [M+H]+ peaks. (FIG. 5B) Analytical RP-HPLC chromatograms of the pure AC253 and cAC253 peptides. (FIG. 5C) MALDI-TOF of Cy51 labeled AC253 and cAC253 peptides showing [M+H]+ peaks. Peptides have extra beta alanine amino acid attached to N-terminus to act as linker. (FIG. 5D) Analytical RP-HPLC chromatograms of the pure Cy5AC253, and Cy5cAC253 labeled peptides.

MALDI-TOF mass spectrometry yielded molecular weights in good agreement with the predicted masses of peptides, linear AC253 showed m/z 2805.2 ([M+H]+ calculated 2085.4), and cAC253 m/z 3008.5 ([M+H]+ calculated 3008.8) (FIGS. 5A-D). Partition coefficient values of peptides proved that both are hydrophilic having log P values of −1.2, and −1.05 for AC253 and cAC253, respectively.

cAC253 was assessed for its antagonist activity at amylin receptor subtype 3 (AMY3) and whether it also retained its neuroprotective properties against Aβ toxicity using two in vitro functional bioassays. AMY3 is the most relevant subtype of amylin receptors in the context of the direct actions of Aβ (and hAmylin) at the level of the cell membrane (Fu et al., 2012). Both peptides of AC253 and cAC253 blocked the hAmylin evoked cAMP increase in a dose-dependent manner. cAC253 was three-fold more potent in inhibiting AMY3 receptor activity in AMY3 stable expression HEK293 cells (AMY3-HEK) (FIG. 4B). The half-maximal inhibitory concentration ($IC_{50}$) for AC253 and cAC253 was approximately 0.85 and 0.3 µM respectively.

Soluble oligomeric Aβ is known to be toxic in neuronal cell cultures. AC253 attenuates $Aβ_{1-42}$ and hAmylin-induced apoptotic cell death in cultured human neurons via its antagonist activity at the AMY3 receptor (Jhamandas et al., 2011). It was examined whether in vitro cAC253 can protect human fetal neurons (HFNs) and N2a cells (a neuronal tumor cell line) from $Aβ_{1-42}$ induced cytotoxicity. Using the MTT and live-dead assays, both peptides were equally effective in attenuating cell death induced by $Aβ_{1-42}$ in a dose-dependent fashion (FIG. 4C-F), confirming that cAC253 retained its amylin receptor antagonist and neuroprotective properties against Aβ toxicity.

The above results indicate that cyclization enhanced AC253 binding to AMY3 expressing cells, and resulted in superior blood brain barrier permeability after a single ip injection compared to linear form of AC253 at therapeutically relevant concentrations. Furthermore, cAC253 showed a seven-fold increase in proteolytic stability ($t_{1/2}$), and better pharmacokinetic profile compared to AC253. In comparison systemically, and a shorter peptide sequence that renders it more cost effective therapeutic agent. cAC253 may be a potent CNS-permeable peptide that holds promise as a therapy for Alzheimer's disease.

An important observation relates to the positive correlation between cAC253 uptake across the blood brain barrier and the expression levels of the amylin receptor in the brain. In hemizygous CTR mice, which exhibit a 50% knocked down of the CTR (and hence amylin) receptor, a significantly reduced cAC253 fluorescent labelling in the brain including the hippocampus was observed compared to wild-type mice that carry a normal complement of amylin receptors. Conversely, for TgCRND8 mice, in which an up-regulation of the amylin receptors has been reported (Jhamandas et al., 2011), cAC253 fluorescence was markedly increased in the same brain regions. Binding of cAC253 to amylin receptors is also supported by the finding that injection of a mixture of Cy5 fluorescently labeled cAC253 and free unlabeled cA253 peptide resulted in a 75% reduction in brain fluorescence levels in comparison to animals injected with the fluorescently labeled cAC253 only. Intense histological staining for CTR along the endothelial cells of the cerebral vessels in TgCRND8 and wild-type mice was observed, suggesting that the amylin receptors may be involved in the brain uptake of the amylin peptide from the vasculature. This notion is supported by studies in the cat, where amylin immunoreactive fibers were shown to innervate cerebral vessels and application of this peptide resulted in a relaxation of ring segments of the middle cerebral artery containing endothelium (Edvinsson et al., 2001).

iii) cAC253 has Enhanced Binding to AMY3 Receptor In Vitro

The in vitro binding efficacy and specificity of cAC253 compared to AC253 were examined in AMY3-HEK cells (Fu et al., 2012) using flow cytometry and fluorescence microscopy. Cy5 near-infrared (NIR)-labeled peptides (AC253, cAC253) were synthesized and characterized using MALDI-TOF mass spectrometry, which displayed molecular weights in agreement with calculated values (TABLE 2).

FIGS. 6A-D show that cAC253 has enhanced specific binding to AMY3 receptor in vitro compared to linear AC253. (FIG. 6A) Flow cytometry histograms comparing Cy5 labeled AC253, and cAC253 peptides (5 µM) for HEK293-AMY3 cells binding and uptake after 60 min incubation in serum free media at 37° C. (FIGS. 6B-C) Graphs showing the dose dependent uptake of Cy5 labeled peptides in HEK293 AMY3 cells and quantification of cell uptake of peptides at 4° C. in presence of cytocholasin D (Cyto-D, an endocytosis inhibitor), and in presence of human amylin (a competitive binding inhibitor). Data are from two independent experiments carried out in triplicate (*p<0.05). (FIG. 6D) Representative fluorescence microscopy images showing Cy5 labeled peptides binding to GFP labeled HEK293 AMY3-expressing cells at 37° C. for 60 min incubation (Scale bar=10 am).

FIG. 7 shows flow cytometry histograms indicating the Cy5.5 labeled AC253 and cAC253 peptides (5 μM) cell binding and uptake in wild type HEK293 cells after 60 min incubation at 37° C.

From flow cytometry assay (FIG. 6A), cAC253 displayed 3-fold enhanced binding and uptake into AMY3-HEK cells compared to AC253 with mean fluorescence intensity of 3300 and 1200 for cAC253 and AC253, respectively. Cell binding to both antagonists increases in a dose-dependent manner with Kd of 1.45±0.5 and 2.6±1.0 μM for cAC253 and AC253, respectively (FIG. 6B). Further increase of peptide concentration beyond 10 μM revealed saturation, suggesting that these peptides bind and interact with the AMY3-HEK cells through a receptor-based mechanism. In wild type HEK293 cells, both antagonists demonstrated a 10-fold decrease in binding and uptake compared to that for AMY3-HEK cells, thus confirming AMY3 binding specificity (FIG. 7). To determine the intracellular delivery mechanisms, the delivery efficiency of the peptides was assessed at different temperatures, 4 and 37° C., and in the presence of cytochalasin D (cytoD), an inhibitor of endocytosis via clathrin-coated pits. Both peptides behaved similarly and a marked decrease in binding and uptake was observed at 4° C. with mean fluorescence intensity of 356.6±35 and 400±75 for cAC253 and AC253, respectively, indicating that peptides cell uptake occurs via an energy dependent endocytic pathway (FIG. 6C). In the presence of cytoD, the cell uptake of both peptides was significantly decreased (3-fold) with mean fluorescence intensity of 1100±100 and 450±50, for cAC253, and AC253, respectively, suggesting that clathrin endocytosis is, at least in part, responsible for the uptake of peptides (FIG. 6C). Binding of the antagonists to AMY3-HEK cells was competitively inhibited when cells were pre-incubated with hAmylin, and peptide cell uptake was partly inhibited with mean fluorescence intensity of 1250±200 and 500±100 for cAC253 and AC253, respectively (FIG. 6C). With fluorescence microscopy we observed strong binding of both peptides to cell membrane of AMY3-expressing HEK cells (FIG. 6D).

iv) cAC253 can Efficiently Penetrate the Blood Brain Barrier

FIGS. 8A-D show cyclic AC253 is a brain permeant amylin receptor antagonist and distributed within the hippocampus. (FIG. 8A): In vivo NIRF brain imaging of Cy5 AC253, and cAC253 peptides compared to saline injected wild type mice at 0, 2, 24 h time points using Kodak imager. (FIG. 8B) Ex vivo images of brains receiving 0.1 mmol in 200 μl saline AC253, or cAC253 peptide compared to saline injected mice (control). (FIG. 8C) Quantification of brain fluorescence intensity after 2 hr ip injection of labeled peptides (n=5 in each group, **p<0.01 * p<0.05). (FIG. 8D) Brain sections from ex vivo experiments (FIG. 8B) showing AC253 and cAC253 fluorescent labeling (red) within the hippocampus. Nuclear staining with DAPI (blue). Scale bar=100 m.

Figure 8D:
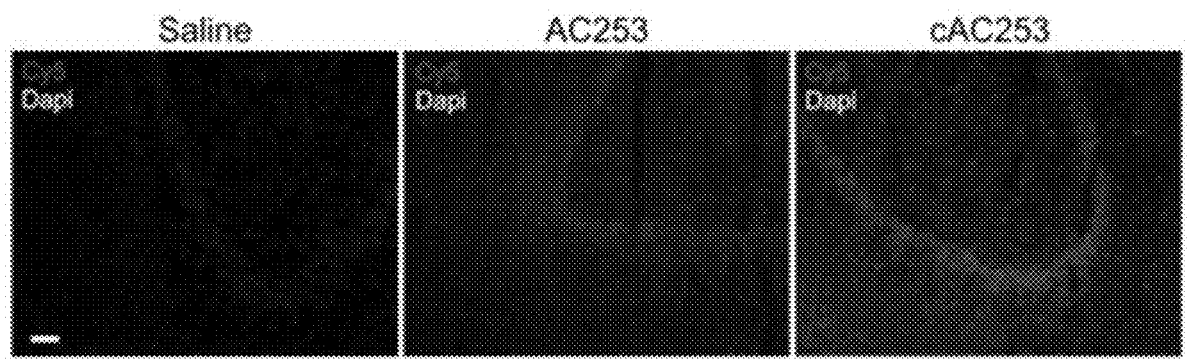

The ability of cAC253 and AC253 to penetrate BBB in wild-type mice was assessed using NIR fluorescence in vivo, and ex vivo imaging. After single intraperitoneal (ip) administration, the fluorescence signal for both peptides was significantly increased in the brain, and it was detectable in brain regions within 10 min post-injection. A peak fluorescence signal was observed at 2 h, which was therefore selected as an optimal time point for further ex vivo experiments. The fluorescence signal slowly washed out, but could still be observed up to 24 h, indicating its retention in the brain parenchyma rather than remaining bound only within the vasculature endothelium (FIG. 8A). To ensure that fluorescence observed was mainly due to the whole peptide, the Cy5 dye was injected alone and brain imaging showed that it could not on its own cross the BBB. These results demonstrate the ability of amylin receptor antagonist peptides (cAC253 and AC253) to penetrate the blood brain barrier when given peripherally. Ex-vivo brain imaging 2 h post ip injection was consistent with the in vivo imaging data, and the signals from peptides injected mice brains were 2.8, and 2-fold higher for cAC253 and AC253, respectively than saline injection. In addition, the signal from cAC253 was 1.4-fold higher than AC253 (FIGS. 8B-C). Interestingly, while the peptides were distributed throughout the entire brain, the fluorescence was strongly localized to the hippocampal region, which also coincides with the localization of amylin receptor expression in the brain (Roth et al., 2013). Histological analysis of ex-vivo imaged brains confirmed that the peptides were mainly accumulated in the hippocampal region (FIG. 8D).

Figure 9A:
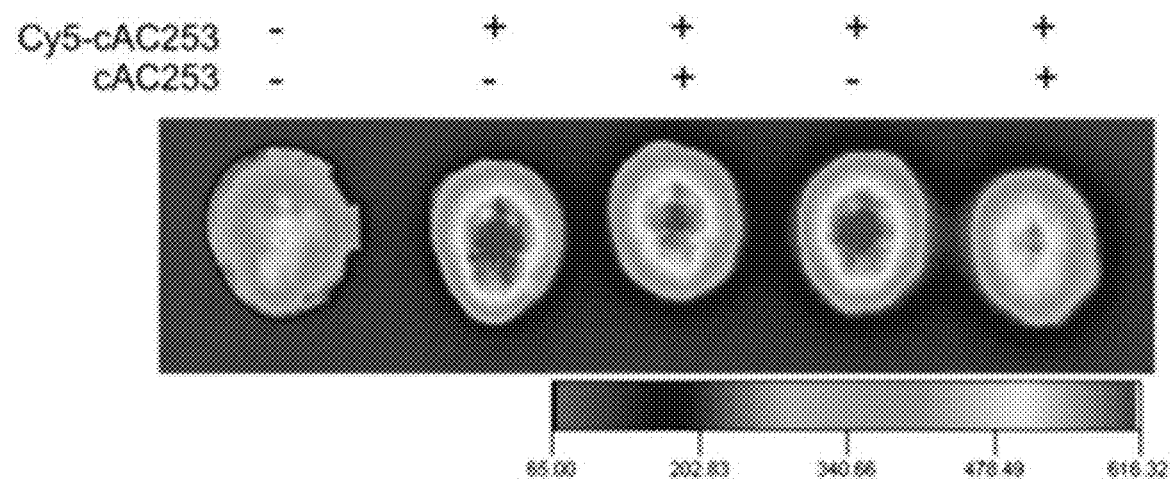
FIGS. 9A-B show ex vivo NIRF fluorescence brain images and quantification.
Figure 9B:
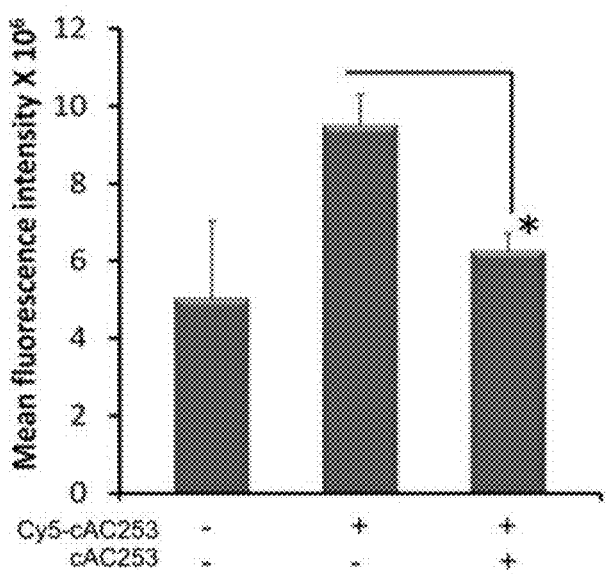

An in vivo competition experiment was performed where mice were injected with Cy5-cAC253 along with a 5-fold excess of unlabeled cA253 peptide. FIGS. 9A-B show (FIG. 9A) representative ex vivo NIRF fluorescence brain images and (FIG. 9B) quantification 2 hr post-ip injection of 40 μg Cy5.5 cAC253 in the presence of 5-fold excess of unlabeled cAC253 (200 μg). (Data values are expressed as mean±SEM of two independent experiments. n=5 in each group, student t test, *p<0.05). The brain fluorescence signal in animals receiving the peptide mixture was significantly reduced (by ~75%) in comparison to the Cy5-cAC253 only. These data support the notion that the brain uptake of these peptides occurs via an amylin receptor based mechanism.

Figure 10A:
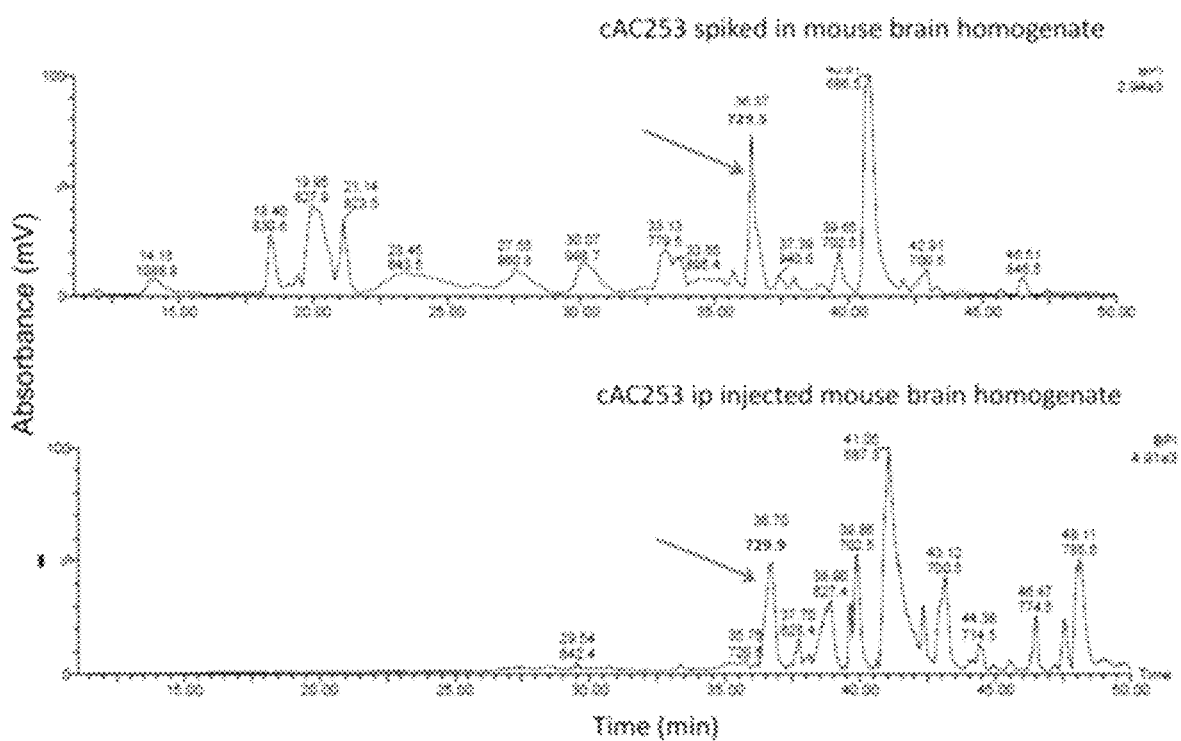
FIGS. 10A-B shows an analytical RP-HPLC profile and multicharged ESI-TOF MS spectrum.
Figure 10B:
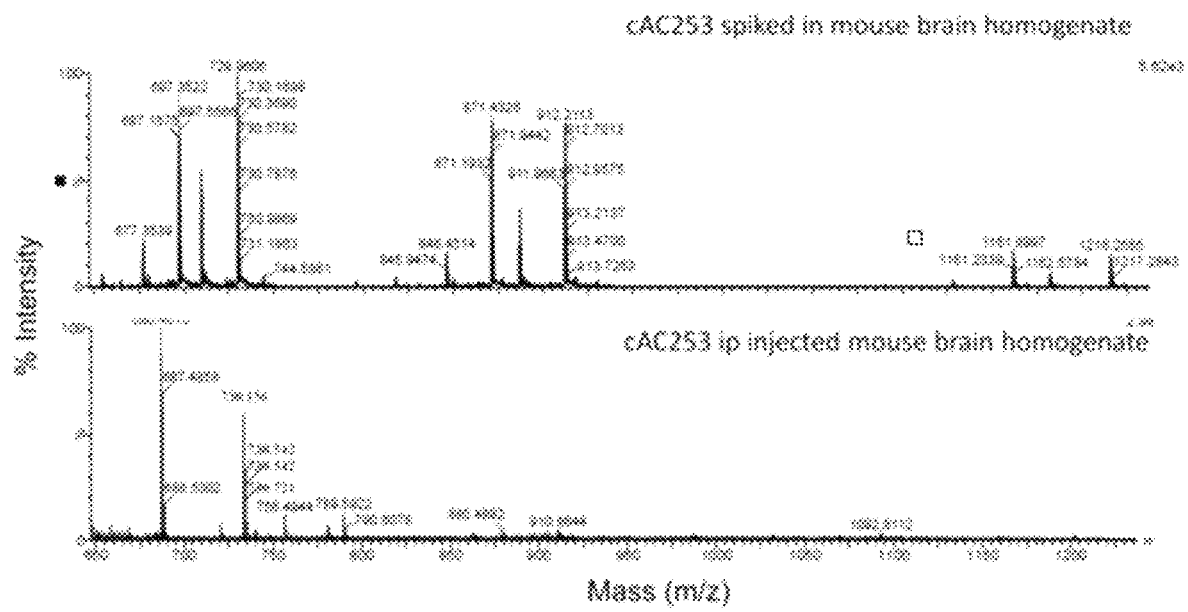

To further confirm if cAC253 peptide is indeed in its intact form in the brain, LC MS/MS was used on brain tissue homogenates. FIG. 10A shows analytical RP-HPLC profile of the purified Cy5cAC253 peptide after spiking in the brain homogenate of saline injected mouse compared to chromatogram of brain homogenate, each received 0.1 mmol Cy5 cAC253, elution time is 36.7 min. FIG. 10B shows multicharged ESI-TOF MS spectrum of brain homogenates of three mice brains 2 hours after ip injection of Cy5.5 cAC253 (0.1 mmol/each mouse). As shown in RP-HPLC chromatograms, consistent with Cy5-cAC253 peak that elutes at 37 min, a similar peak was identified in the brain homogenate from animals that received cAC253. Mass spectrometry of the eluted peak at the denoted retention time revealed a molecular weight of 730.156 ([M+5H]$^+$ calculated 730.512), consistent with that of the full length peptide and supporting the conclusion that the cAC253 peptide intact.

Figure 11:
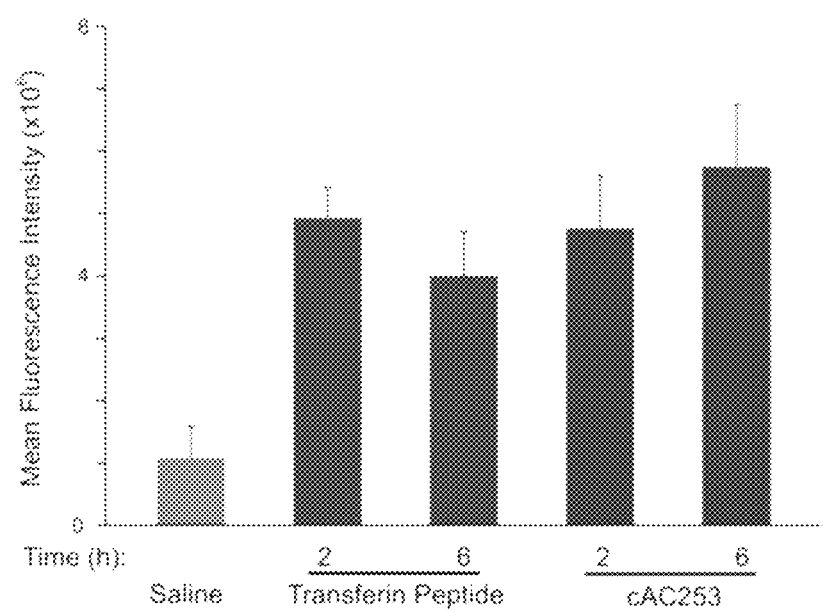
FIG. 11 is a bar graph showing the quantitative fluorescence intensity of ex-vivo brain imaging after particular injections.

The ability of peptide drugs, when administered systemically, to achieve therapeutic concentrations in brain is a significant challenge. Accordingly, the brain concentrations of cAC253 peptide were compared to that of T7 peptide (HAIYPRH, SEQ ID NO: 17) that utilizes the transferrin receptor to penetrate the BBB and achieve therapeutic concentrations in the brain (Han et al., 2010; Wu et al., 2015). FIG. 11 is a bar graph showing the quantitative fluorescence intensity of ex-vivo brain imaging after injection single dose of 0.01 mmol Cy5.5 cAC253 peptide compared to mice injected with the same concentration of T7 transferin peptide HAIYPRH 2, 6 hr post-ip injection. All graphical values are expressed as mean±SD of two independent experiments. n=3 in each group. Ex-vivo brain fluorescence signal from AC253 was comparable to the fluorescence of T7 peptide injected group after 2 h post-injection, while at 6 h the fluorescence level of cAC253 was further increased by 20% more while T7 started to show rapid clearance from the brain, thus supporting a longer half-life for cAC253 than T7 (FIG. 11).

Figure 12B:
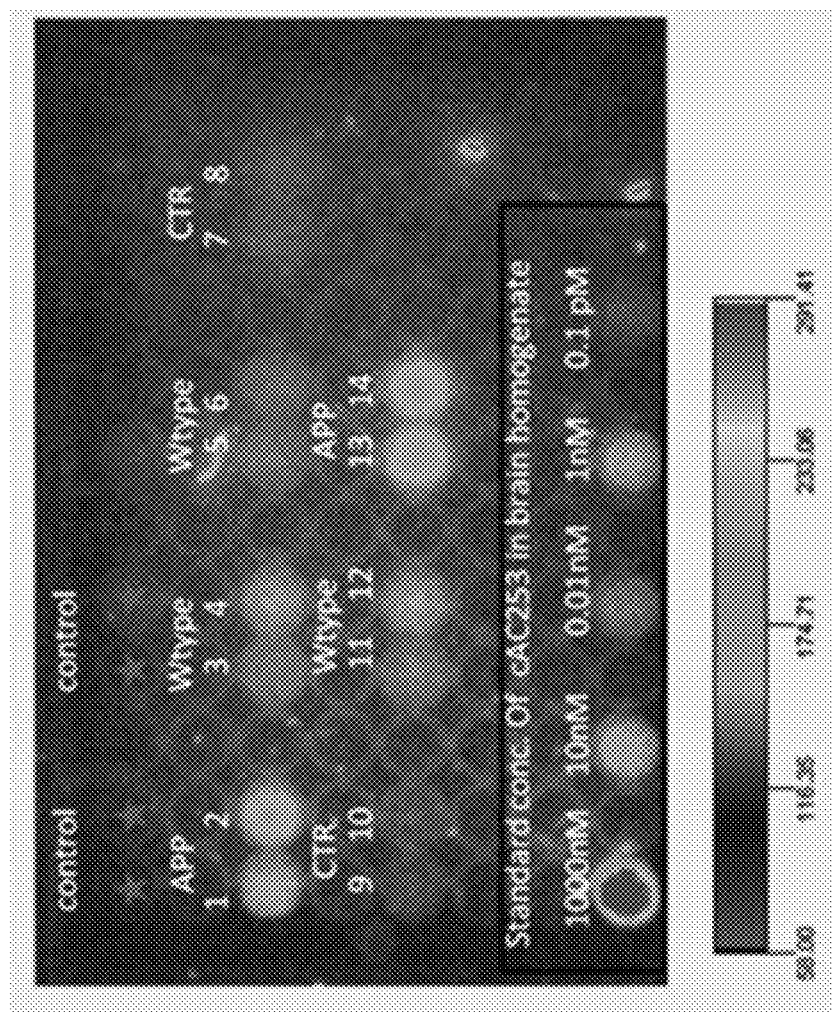
FIG. 12A-B show fluorescence images of Eppendorf tubes with mice brain homogenates, and determination of peptide concentration in brain homogenates.
Figure 12A:
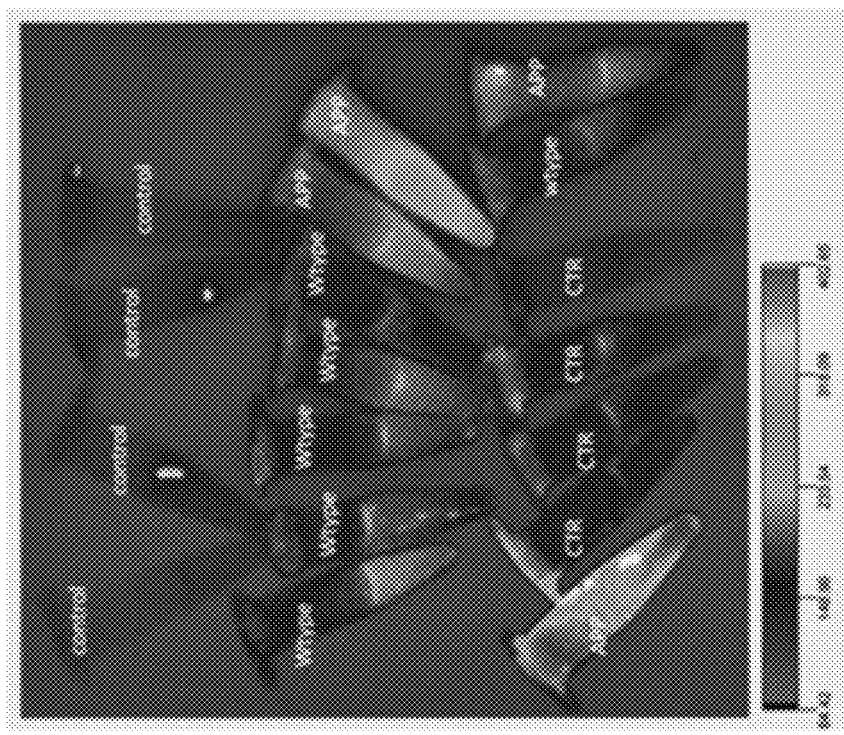

FIG. 12A shows a representative fluorescence image of Eppendorf tubes with the mice brain homogenates that received (400 µg, 0.1 mmol in 200 µl saline) Cy5.5 cAC253 (wild type, het CTR 50% knocked down, and APP transgenic) after 2 h post ip injection compared to control wild type mice that received saline. Fluorescence in APP mice showed the highest fluorescence signal followed by wild type mice, followed by CTR knocked down mice. FIG. 12B shows determination of cAC253 peptide concentration in brain homogenates in a 96-well microplate by comparing the fluorescence to standard concentration of Cy5.5 cAC253 in saline injected mice brain homogenate. The brain cAC253 concentration after injecting 40 µg Cy5-AC253 was estimated to be in the range of 10-100 nM, a level equal to 0.1% of the injected dose. These estimates of brain levels are comparable to reported values for bioactive peptides such as amylin or insulin (Banks et al., 1995; 1998).

v) cAC253 In Vitro and In Vivo Pharmacokinetics

Figures 13A, 13B:
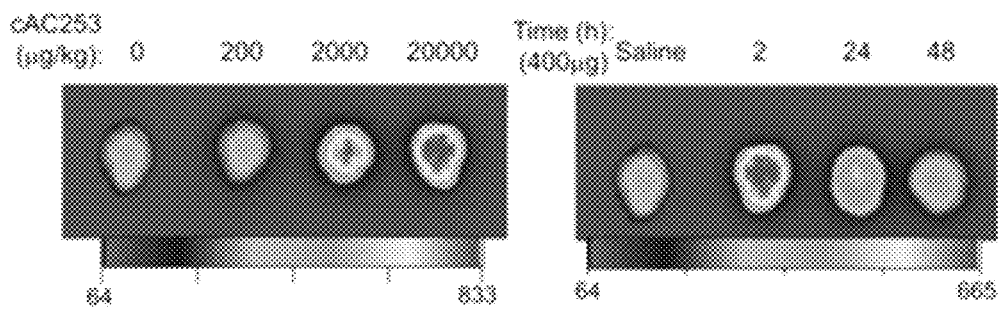
FIG. 13A-F show ex vivo fluorescence brain images and quantification of data.
Figures 13C, 13D:
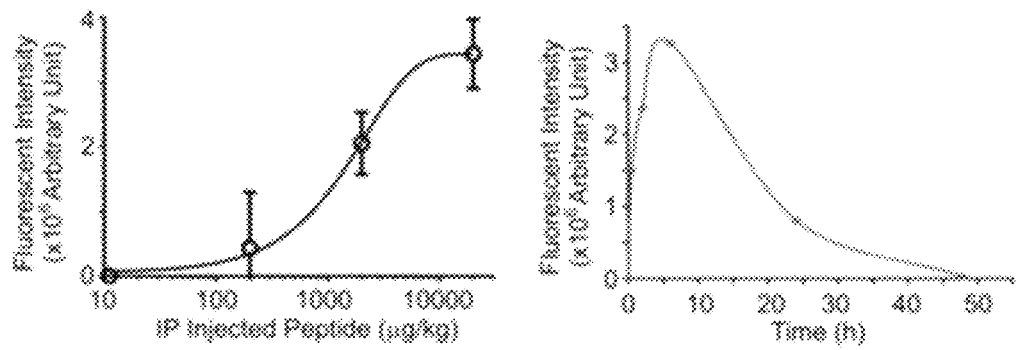

The pharmacokinetic profile and the stability of cAC253 were assessed in vitro and in vivo. FIGS. 13A-F show that cyclic AC253 demonstrates superior pharmacokinetic profile, and proteolytic stability compared to AC253. (FIGS. 13A-D) Representative ex vivo fluorescence brain images and quantification of data for cAC253 brain accumulation at different doses and time points after a single ip injection of 0.1 mmol in 200 µl saline (400 µg) (n=3). (FIG. 13E) In vitro stability cAC253 peptide in human serum compared to AC253 at 37° C. The amount of intact peptide in human serum at different time points was estimated using RP-HPLC. (FIG. 13F) Histograms showing bio-distribution of cAC253 peptides in organs of wild type mice at 2 hr post injection of 0.1 mmol in 200 µl saline of the peptide (n=3). cAC253 fluorescence levels were analyzed in wild-type mice that received 0, 0.2, 2, 20 mg/kg as a single ip dose after 2 h. Cy5-cAC253 accumulation appears to be concentration dependent, and saturable since a dose increment from 2 to 20 mg/kg achieved a steady state of increased fluorescence, which suggests a receptor mediated brain uptake of this peptide (FIGS. 13A, 13C). The time dependence for the peptide to clear from the brain after injecting 20 mg/kg of the peptide ip was determined (FIGS. 13B, 13D). Cy5-cAC253 fluorescence signal in the brain reached its maximum at 6 h after which it slowly declined with an estimated half-life of 16 h.

Figure 14:
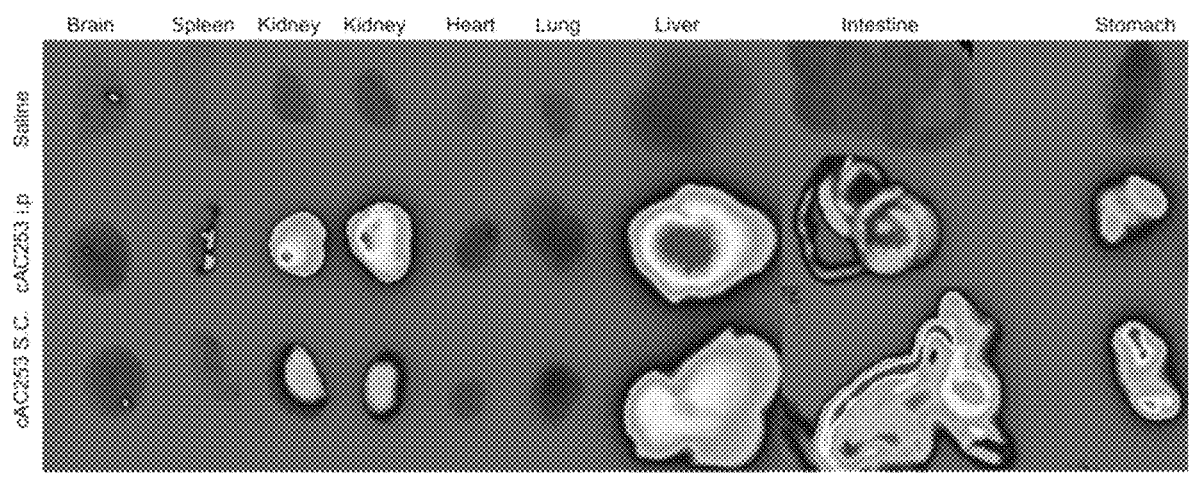
FIG. 14 shows a representative ex vivo image showing fluorescence signals in mice organs.

Bio-distribution evaluation of cAC253 in different organs (liver, kidney, spleen, lung, heart, brain, stomach and intestine) was investigated 2 h after injecting 20 mg/kg peptide. FIG. 14 shows a representative ex vivo image showing fluorescence signals in mice organs (heart, lung, liver, kidney, spleen, stomach intestine) ip compared to sc (0.1 mmol in 200 µl saline, 400 µg) 2 hr after Cy5.5 cAC253 injection. Fluorescence signal was mainly observed in the eliminating organs such as kidneys, liver and in the injection sites (intestine). Less uptake was detected in brain and lungs. Ex vivo fluorescence signals from tissues indicated that cAC53 was distributed within all organs examined although uptake in lung, spleen, and heart was considerably less compared to the kidney and the liver, which showed a strong NIR fluorescence intensity in keeping with renal and hepatic clearance of the peptide (FIGS. 13D, 14).

Figures 13E, 13F:
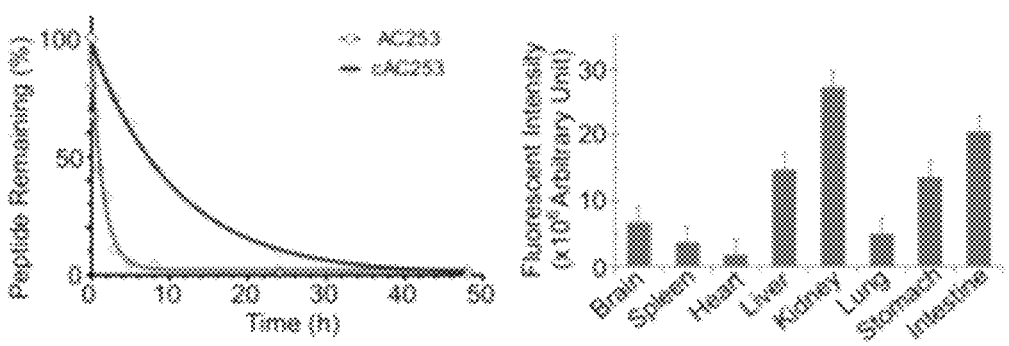

The influence of cyclization on the proteolytic stability of cAC253 compared to AC253 was assessed. Cyclic-AC253 was found to be 7 times more stable in human serum compared to AC253 with half-lives of 7 and 1 h, respectively. This confirms that cyclization of AC253 enhanced its stability and conferred protection from proteolytic cleavage, thus increasing the amount of peptide reaching the brain through the systemic circulation (FIG. 13E). By assessing the main degradation fragments in both peptides with MALDI-TOF, both peptides were found to be cleaved at the basic arginine amino acids R3, R10 and R16. In mouse liver microsomes, both peptides were rapidly degraded within 5 min, with fragmentation patterns showing that peptides got cleaved one amino acid after the other from the N-terminal end of the peptide chain, which mostly accounts for aminopeptidase or N-terminal dipeptidylpeptidase IV activity. It appears that the C-terminal amide prevented carboxipeptidases from digesting the peptide (data not shown).

vi) cAC253 Targets the CTR Receptor In Vivo

To study the connection between the expression level of the amylin receptor, and the degree of cAC253 brain permeability, peptide brain fluorescence signal was compared in two genetically engineered mouse models that express differing levels of the CTR receptor. Two engineered mouse resources were used: hemizygous CTR mice that exhibit 50% CTR expression ("hetCTR") and hence 50% reduction in the functional amylin receptor (Davey et al., 2008), and transgenic APP695-overexpressing CRND8 (TgCRND8) mice known to have up-regulation of the amylin receptor (Jhamandas et al., 2011).

Figure 15A:
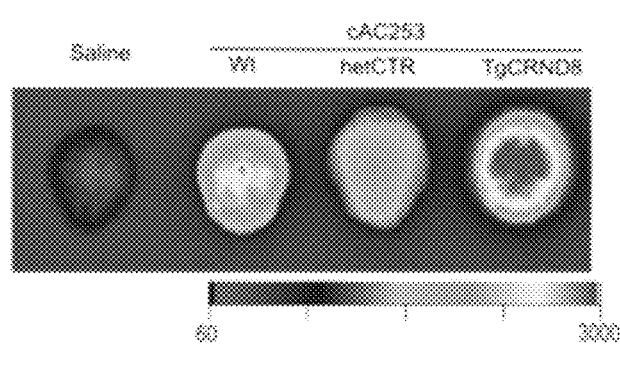
FIGS. 15A-C show brain images, quantification of data, and brain sections.
Figure 15B:
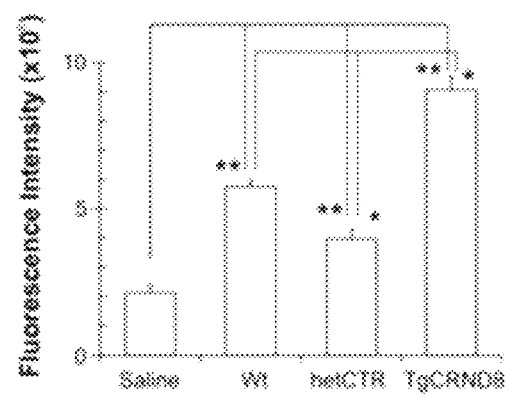
Figure 15C:
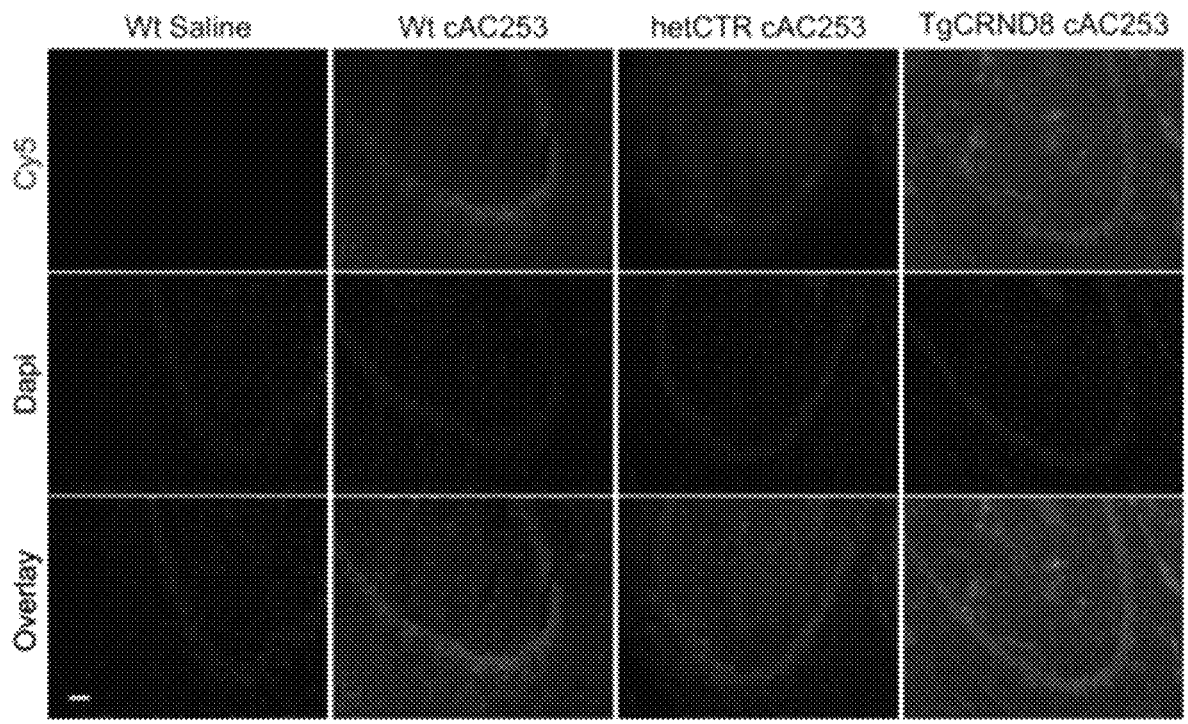

FIGS. 15A-B show that cyclic AC253 brain uptake correlates with expression of amylin receptor levels in the brain (FIG. 15A): Brain images from wild-type (Wt), heterozygous CTR knockdown (50% depletion of amylin receptors) or TgCRND8 (that over-express amylin receptors) mice 2 hr after receiving equimolar ip injections (0.1 mmol in 200 µl saline) of cAC253. (FIG. 15B) Quantification of data for cAC253 brain accumulation in the three mice genotypes. (n=5 in each group, *p<0.05, **p<0.01) (FIG. 15C) Brain sections from the three mouse genotypes showing fluorescent labeling through the hippocampus following a single ip injection of Cy5 labeled cAC253 (Scale bar=100 am).

After 2 h ip injection, ex vivo brain imaging results demonstrated that the fluorescence of cAC253 in brains of TgAPP mice increased by 45% compared to wild-type age-matched controls (FIGS. 15A-B). However, for hetCTR mice, the brain fluorescence decreased by 30% compared to that of wild type mice (FIGS. 15A-B). These data therefore indicate that the amount of cAC253 uptake and accumulation positively correlates with the level of amylin receptor expression in the brain. These observations were further confirmed by immunohistochemical examination of brain sections from the two transgenic mouse models, which showed that the amount of cAC253 labeled peptide within the hippocampus is correlated to the level of CTR expression (FIG. 15D).

Figure 16A:
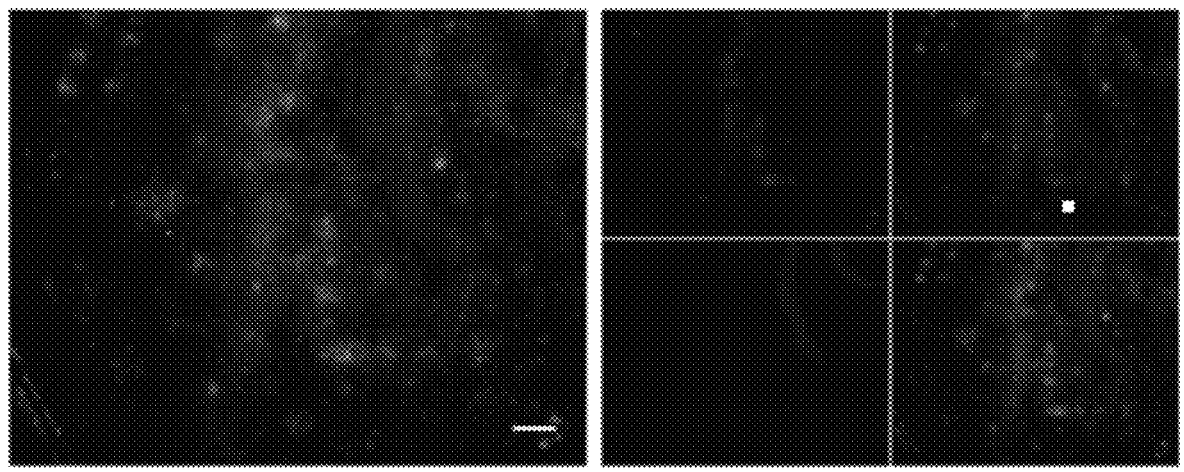
FIGS. 16A-B show fluorescence microscopy images.
Figure 16B:
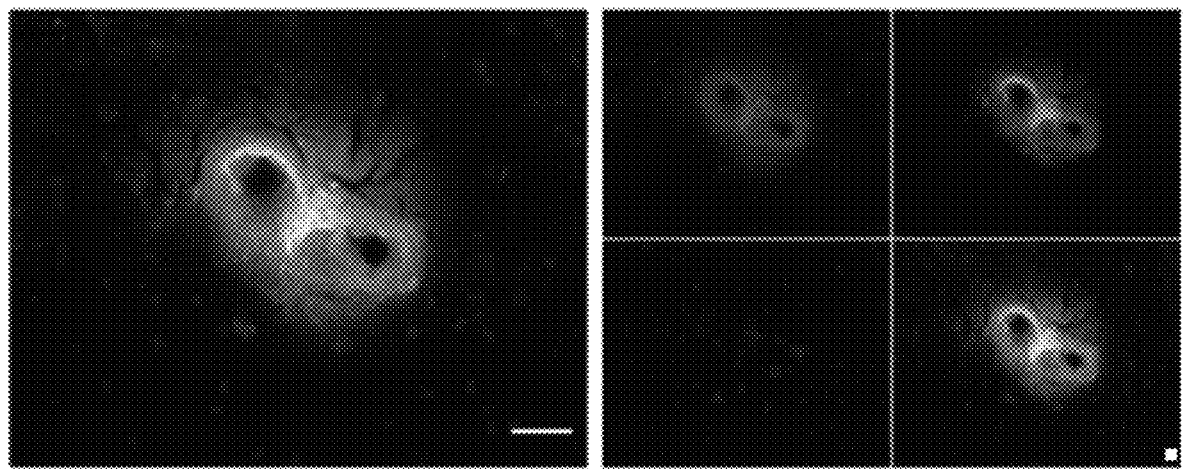

FIGS. 16A-B show wild type mice brains sections which received cAC253 are immunofluorescently stained for CTR (FIG. 16A) Images taken in the hippocampus using fluorescence microscope showed that CTR staining (green) are co-localized with Cy5.5 cAC253 peptide (red), and, interestingly, the CTR staining is co-localized with the Aβ plaques in mouse brain (scale bar 100 µm). (FIG. 16B) Images showing CTR localization (intense green) in the capillary cerebral vessels co-localized with cAC253 peptide which highlight its role in brain uptake (scale bar 20 μm). CTR is co-localized with the labeled cAC253. Furthermore, amyloid plaques in TgCRND8 mice showed both the amylin receptor and the labeled peptide to share a close anatomical relationship with amyloid in the brain tissue, frequently being embedded within the plaques. Examination of histological sections also revealed intense CTR staining along the endothelial cells of the cerebral vessels. Without being bound by any theory, the amylin receptors most likely play a role in the brain uptake of the peptide from the vasculature.

Fourteen peptide fragments of AC253 (designated as R1-R14, Table 1) were synthesized. The effects of the peptide fragments on human amylin-evoked depression of LTP were examined in wild-type (Wt) mouse hippocampal brain slices.

Figure 17A:
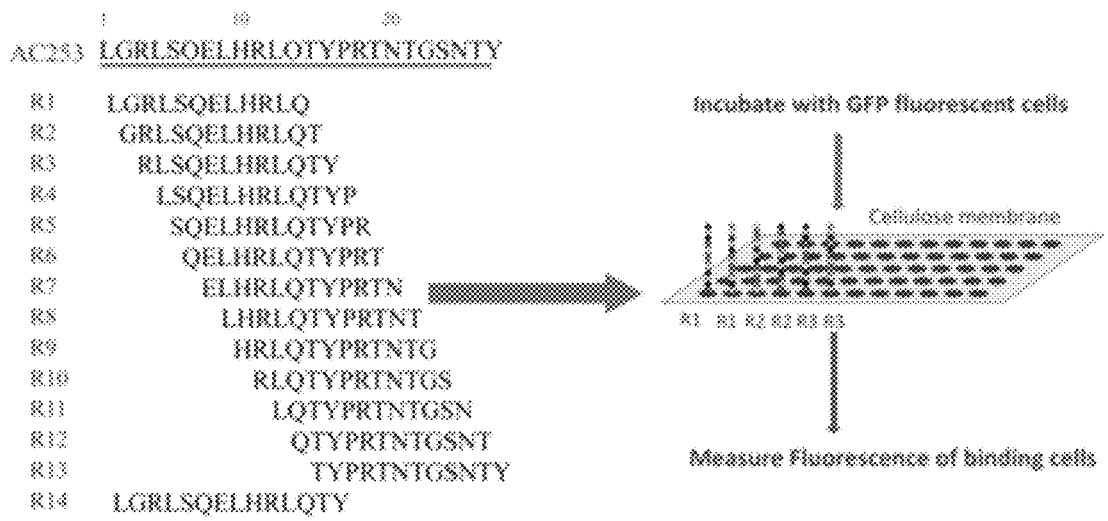
FIGS. 17A-C show AC253 based peptide library design, membrane showing fluorescence, and fluorescence quantification. The sequences in FIG. 17A from top to bottom are set forth in SEQ ID Nos: 1 and 3-16.
Figure 17B:
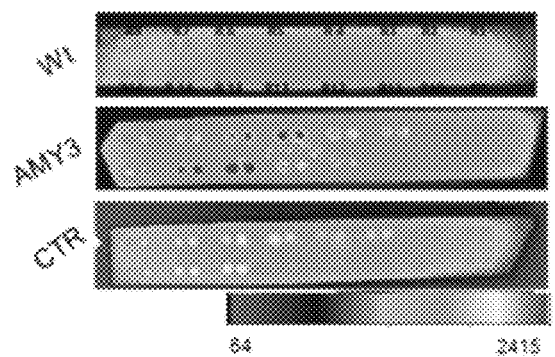
Figure 17C:
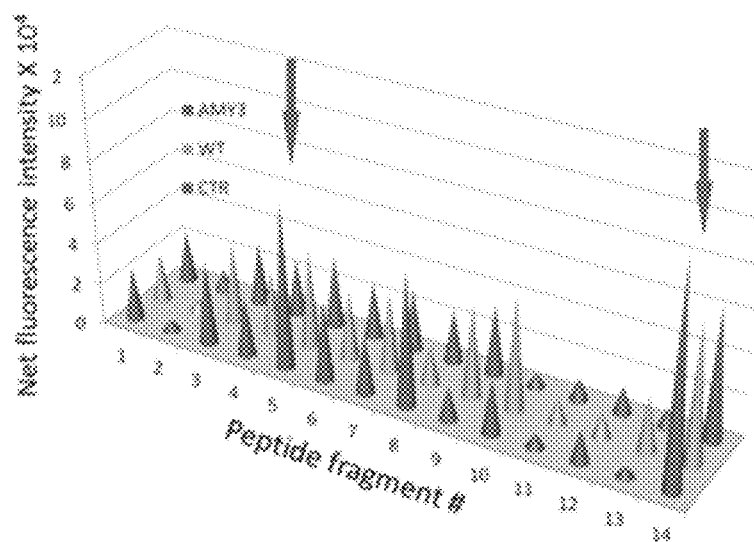
Figure 18A:
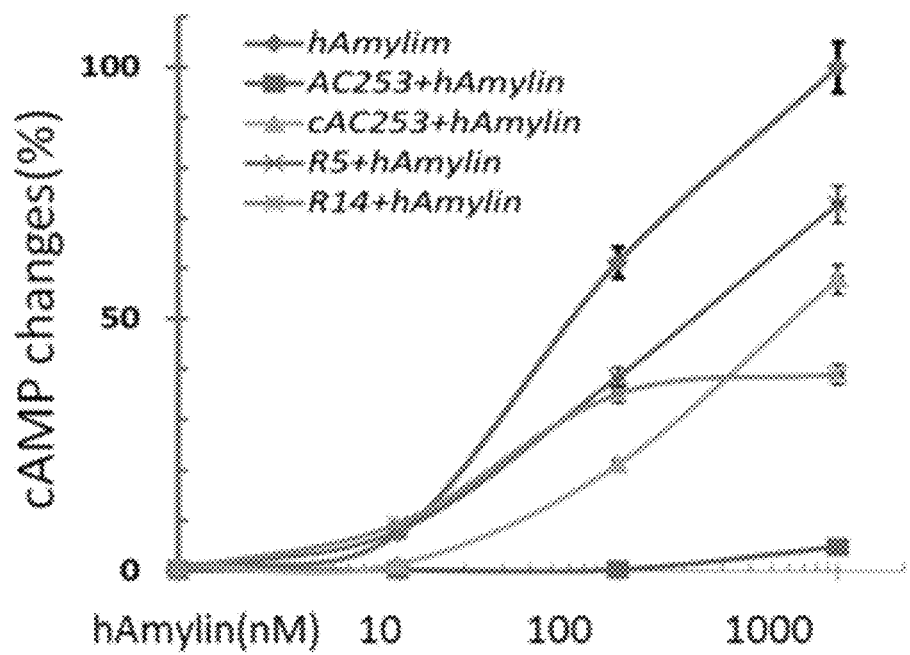
FIGS. 18A-B show graphs related particularly to activity of peptides R5 and R14.
Figure 18B:
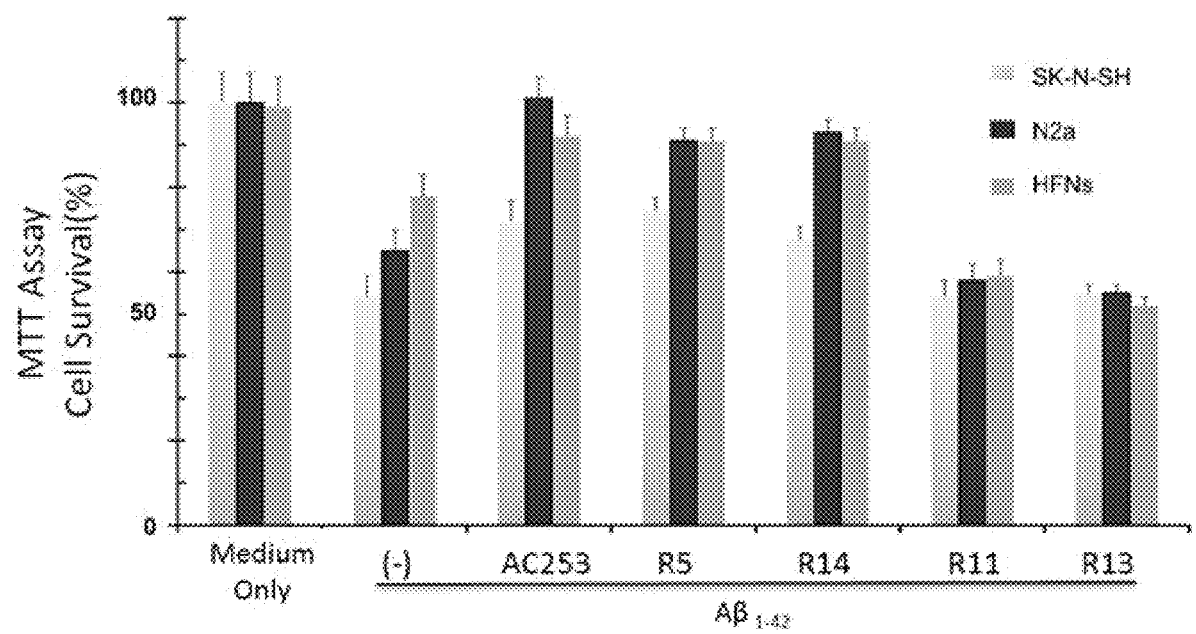

Library screening identifies R5 and R14 fragments with significant binding to AMY3 cells and equipotent antagonistic activity to full length AC253 (FIGS. 17A-C and 18A-B). FIGS. 17A-C show (FIG. 17A) AC253 based peptide library design (12-14 amino acid sequences), peptides were synthesized onto cellulose membrane, each in duplicate, followed by incubation with cells ($4 \times 10^6$) for 4 hrs. (FIG. 17B) Membrane showing fluorescence of AMY3 specifically binding peptide fragments compared to Wt, and calcitonin expressing cells (CTR). (FIG. 17C) Fluorescence quantification shows that peptides R5 (12 aa), and R14 (14 aa) have the most significant binding to HEK293-AMY3 cells compared to other library fragments. FIGS. 18A-B show (FIG. 18A) peptides R5 and R14 were 2-3 times as potent as AC253 in inhibiting hAmylin induced generation of cAMP due to AMY3 activation in AMY3-HEKcells, and (FIG. 18B) both fragments block the effect of $A\beta_{1-42}$ (20 μM) in activation of AMY3 which triggers cell death in human fetal neuronal cells, and neuroblastoma cells (N2a, SK-N-SH) as shown in MTT cytotoxicity assay.

Figure 19A:
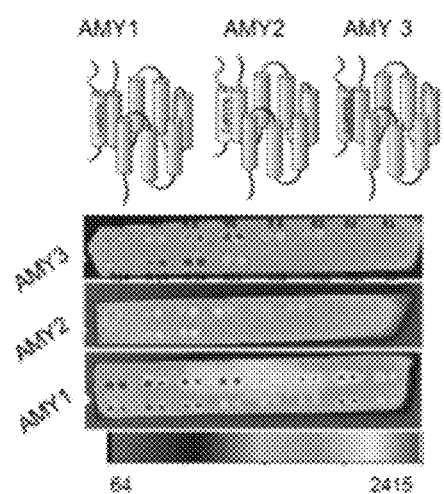
FIGS. 19A-C show results from membrane screening, fluorescence quantification, and flow cytometry cell uptake studies.
Figure 19B:
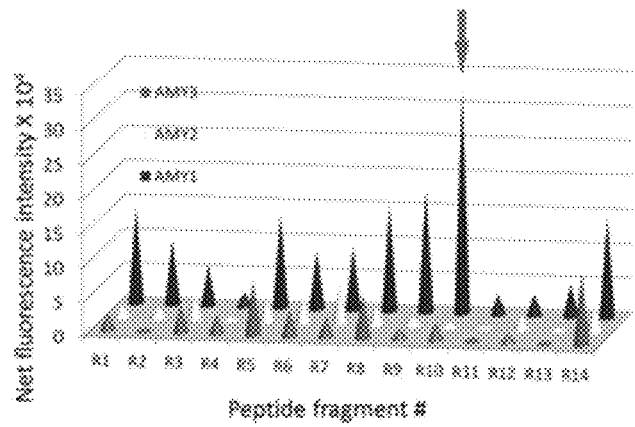
Figure 19C:
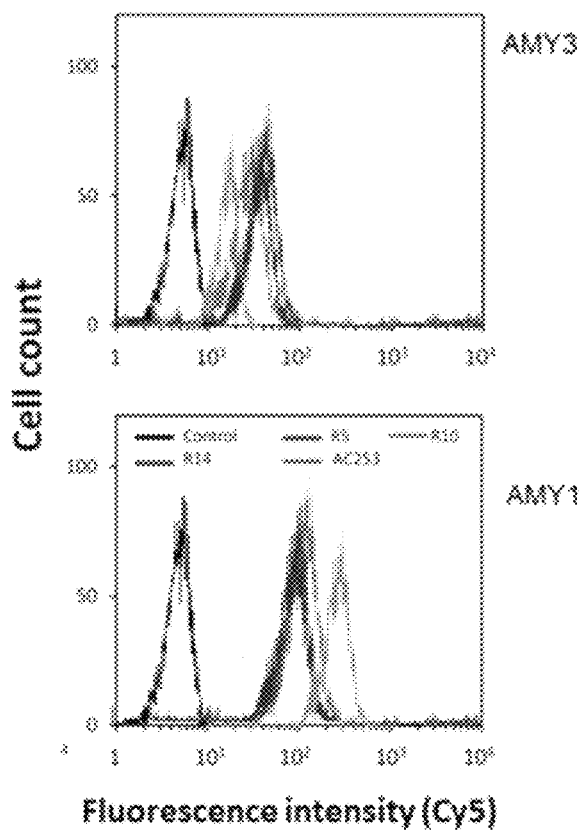

Library screening against amylin receptor subtypes 1-3 transfected cells is shown in FIGS. 19A-C. FIGS. 19A-C show: (FIG. 19A) membrane screening with different AMY1-3 subtypes shows fragments significant binding to both AMY1, and AM3 compared to AMY2; (FIG. 19B) fluorescence quantification shows that R10 is an AMY1 specific peptide; and (FIG. 19C) flow cytometry cell uptake studies demonstrated that R5 and R14 (10 μM) peptides have selective and significant specific binding to HEK293-AMY3 cells as well as AMY1 and similar to AC253 after incubation with at 37° C. for 60 min. Cell uptake histogram showed 3 fold increase in specific binding of R10 to AMY1 compared to other fragments.

Figure 20A:
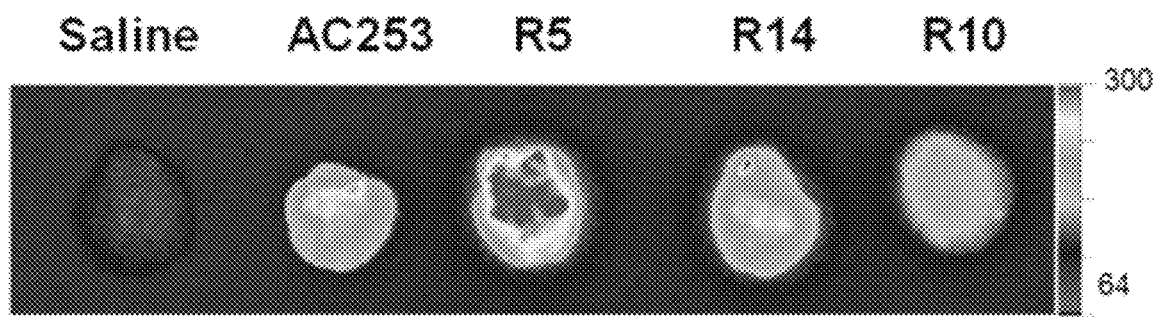
FIGS. 20A-C show ex vivo brain imaging, brain sections from ex vivo brain experiment, and imaging of brains.
Figure 20B:
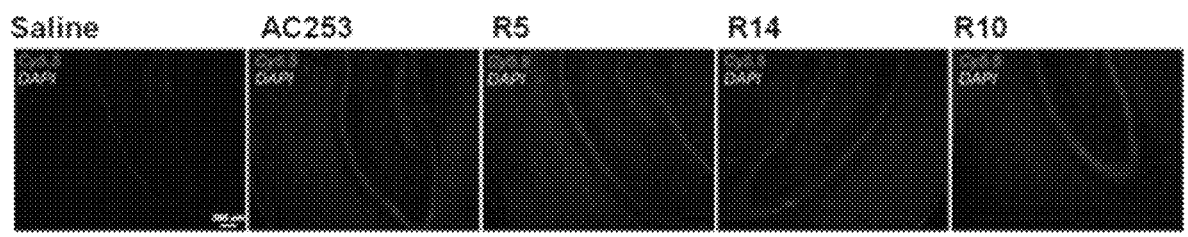
Figure 20C:
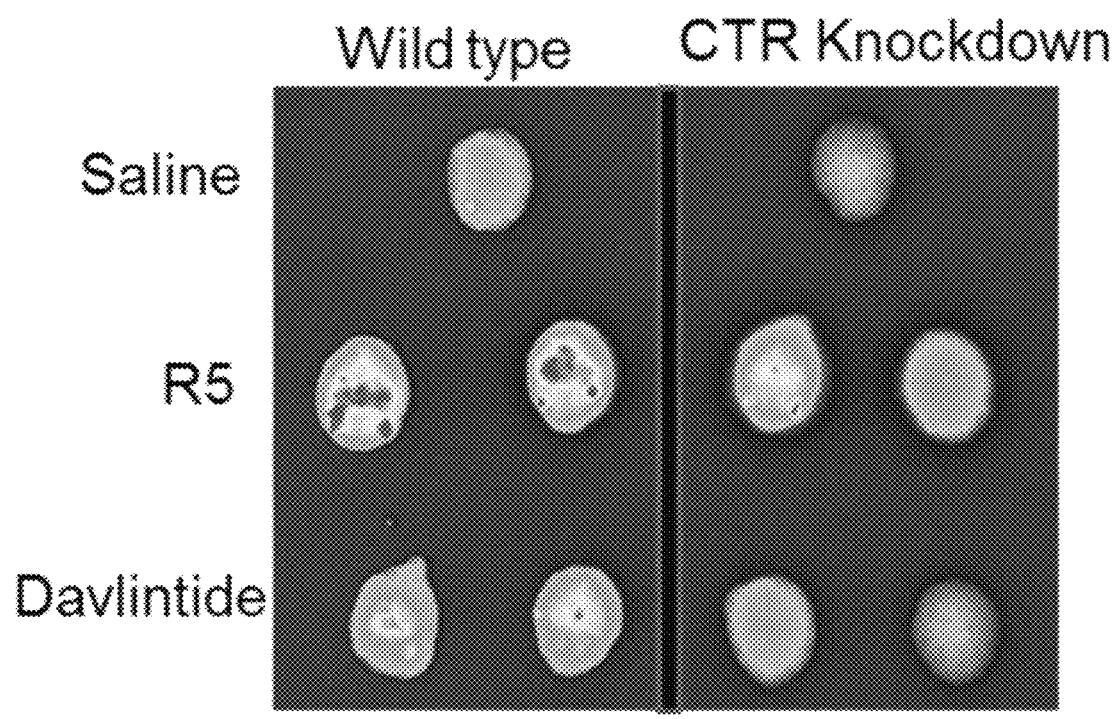

Fragment R5 has superior blood brain barrier permeability in vivo after ip administration and its brain uptake is proportional to the degree of amylin receptor expression. FIGS. 20A-C show (FIG. 20A) ex vivo brain imaging showed that all peptide fragments can penetrate the blood brain barrier 2 hr post-ip injection in wild-type mice, and R5 peptide has marked increase in brain permeability compared to AC253. Peptides show more in the hippocampal and cortical regions, which coincides with the amylin receptor localization in the brain; (FIG. 20B) brain sections from ex vivo brain experiment show the localization of peptides in hippocampus, a region where amylin receptors are present; and (FIG. 20C) wild-type (Wt), heterozygous CTR knockdown (50% depletion of amylin receptors) mice received ip injections of R5 or Davlintide (0.1 mmol); imaging of the intact brain at 2 hr post-injection showed marked brain permeability of R5. In comparison to Wt mice, CTR (amylin receptor) knockdown mice show reduced peptide concentrations in the brain, particularly in the hippocampal region.

Figure 21A:
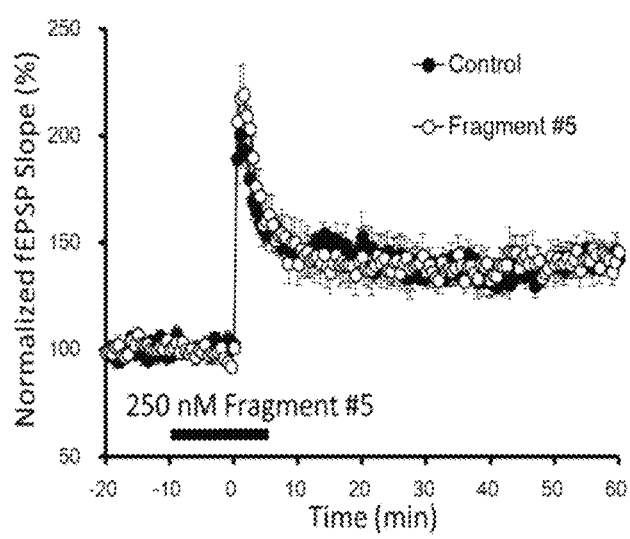
FIGS. 21A-F show images of mice hippocampal slices.
Figure 21B:
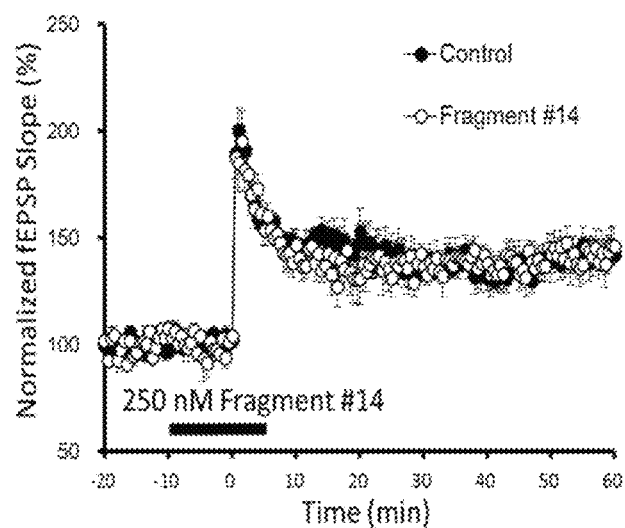
Figure 21C:
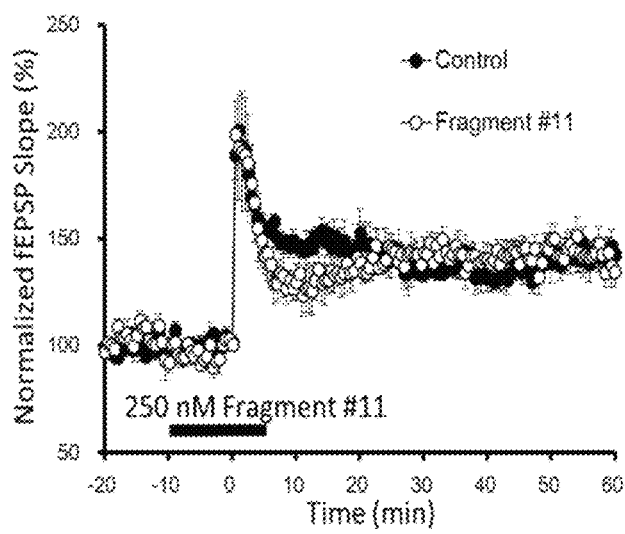
Figure 21D:
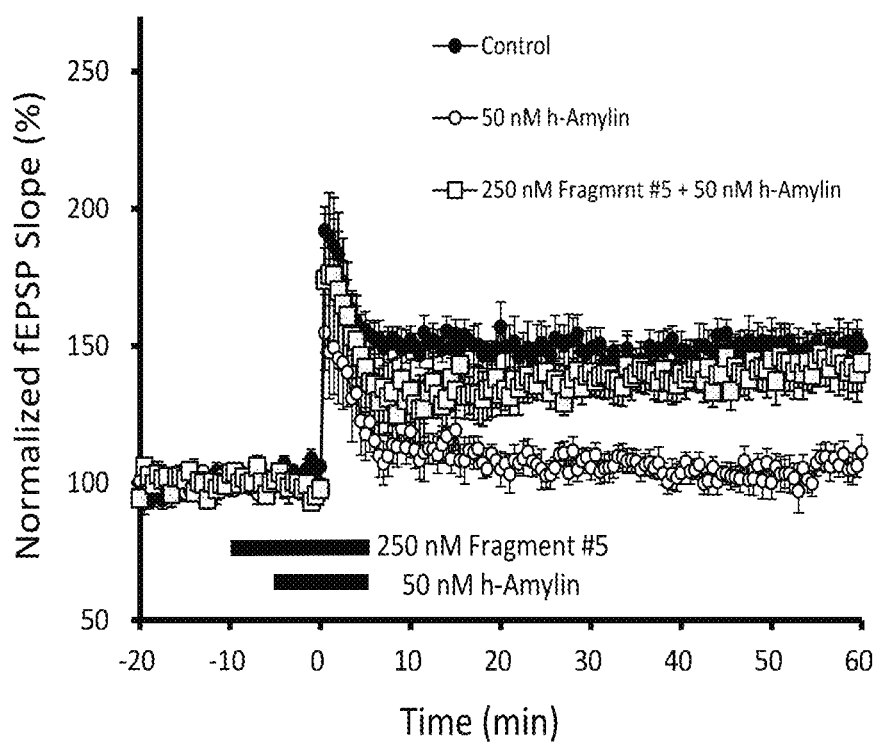
Figure 21E:
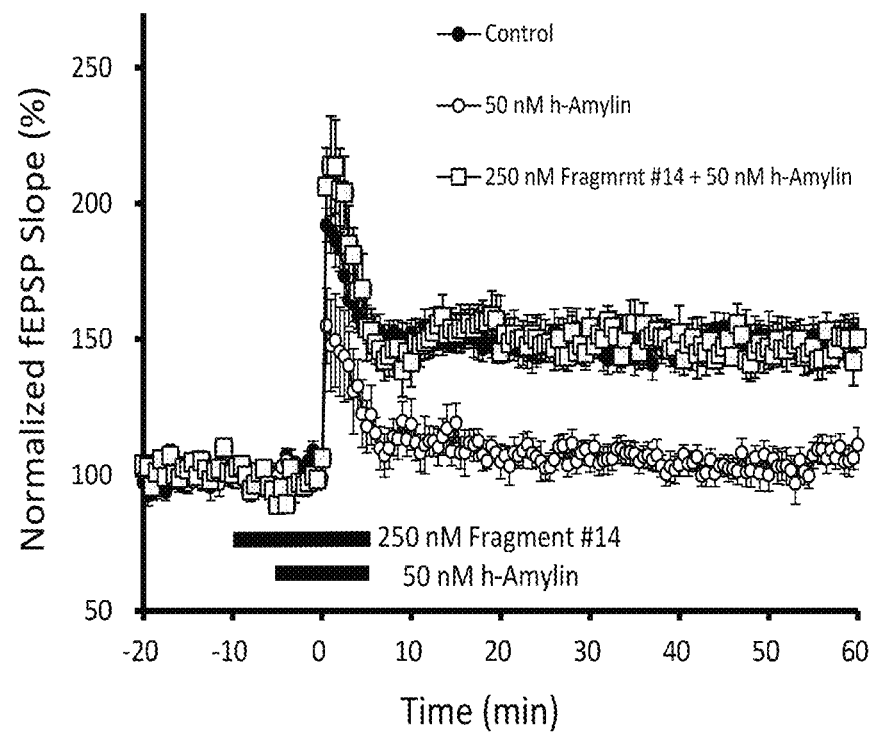
Figure 21F:
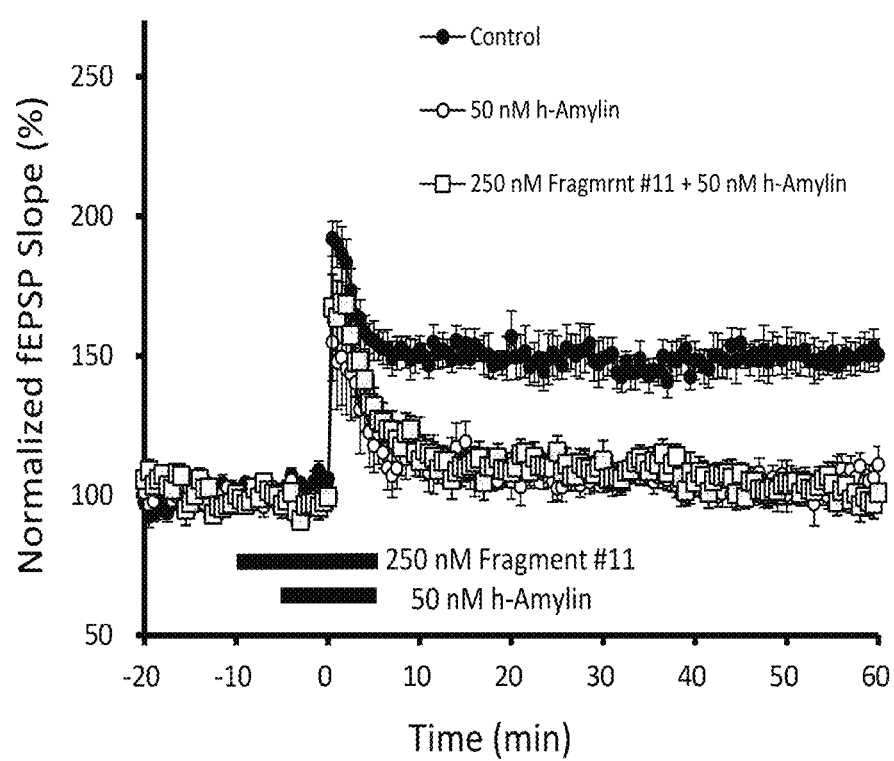

R5 and R14 both reverse h-Amylin depression of hippocampal long-term potentiation (LTP) in mice hippocampal slices. FIGS. 21A-F show (FIGS. 21A-C) R5 and R14 (250 nM) did not impair LTP in hippocampal slice, and did not show reductions in LTP; (FIGS. 21D-F) FIGS. 21D-F show reductions in LTP with application of 50 nM h-Amylin, which is significantly reversed in the presence of R5 and R14 (250 nM). Peptides were perfused 5 min prior to 50 nM h-Amylin application (n=6 slices from five mice per group).

REFERENCES

All publications mentioned herein are incorporated herein by reference (where permitted) to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Abedini A, Schmidt A M. Mechanisms of Islet Amyloidosis Toxicity in Type 2 Diabetes. FEBS letters. 2013; 587: 1119-27.

Ahmed S, Mathews A, Byeon N, Lavasanifar A, and Kaur K. Peptide Arrays for Screening Cancer Specific Peptides, Anal. Chem., 2010, 82 (18), 7533-7541.

Banks W A, Kastin A J, Maness L M, Huang W, Jaspan J B. Permeability of the blood-brain barrier to amylin. Life Sci. 1995; 57:1993-2001.

Banks W A, Kastin A J. Differential Permeability of the Blood-Brain Barrier to Two Pancreatic Peptides: Insulin and Amylin. Peptides. 1998; 19:883-9.

Bateman R J, Xiong C, Benzinger T L S, Fagan A M, Goate A, Fox N C, et al. Clinical and Biomarker Changes in Dominantly Inherited Alzheimer's Disease. N Engl J Med. 2012; 367:795-804.

Chishti M A, Yang D-S, Janus C, Phinney A L, Home P, Pearson J, et al. Early-onset Amyloid Deposition and Cognitive Deficits in Transgenic Mice Expressing a Double Mutant Form of Amyloid Precursor Protein 695. J Biol Chem. 2001; 276:21562-70.

Danysz W, Parsons C G. Alzheimer's disease, β-amyloid, glutamate, NMDA receptors and memantine-searching for the connections. Br J Pharmacol. 2012; 167:324-52.

Davey R A, Turner A G, McManus J F, Chiu W S M, Tjahyono F, Moore A J, et al. Calcitonin Receptor Plays a Physiological Role to Protect Against Hypercalcemia in Mice. J Bone Miner Res. 2008; 23:1182-93.

Di L. Strategic Approaches to Optimizing Peptide ADME Properties. The AAPS Journal. 2014; 17:134-43.

Di Pardo A, Maglione V, Alpaugh M, Horkey M, Atwal R S, et al (2012) Ganglioside GM1 induces phosphorylation of mutant huntingtin and restores normal motor behavior in Huntington disease mice. Proc Natl Acad Sci USA 109 (9):3528-3533.

Edvinsson L, Goadsby P J, Uddman R. Amylin: Localization, Effects on Cerebral Arteries and on Local Cerebral Blood Flow in the Cat. Scientific World Journal. 2001; 1:168-180.

Fu W, Ruangkittisakul A, MacTavish D, Shi J Y, Ballanyi K, Jhamandas J H. Amyloid β (Aβ) Peptide Directly Activates Amylin-3 Receptor Subtype by Triggering Multiple Intracellular Signaling Pathways. J Biol Chem. 2012; 287:18820-30.

Han L, Huang R, Liu S, Huang S, Jiang C. Peptide-Conjugated PAMAM for Targeted Doxorubicin Delivery to Transferrin Receptor Overexpressed Tumors. Mol Pharm. 2010; 7:2156-65.

Hardy J, Selkoe D J. The Amyloid Hypothesis of Alzheimer's Disease: Progress and Problems on the Road to Therapeutics. Science. 2002; 297:353-6.

Hardy J. The amyloid hypothesis for Alzheimer's disease: a critical reappraisal. J of Neurochem. 2009; 110:1129-34.

Hay D L, Christopoulos G, Christopoulos A, Poyner D R, Sexton P M. Pharmacological Discrimination of Calcitonin Receptor: Receptor Activity-Modifying Protein Complexes. Mol Pharmacol. 2005; 67:1655-65.

Hay D L, Poyner D R, Sexton P M. GPCR modulation by RAMPs. Pharmacol Ther. 2006; 109:173-97.

Husmann K, Sexton P M, Fischer J A, Born W. Mouse receptor-activity-modifying proteins 1, -2 and -3: amino acid sequence, expression and function. Molecular and Cellular Endocrinology. 2000; 162:35-43.

Janus C, Pearson J, McLaurin J, Mathews P M, Jiang Y, Schmidt S D, et al. A[beta] peptide immunization reduces behavioural impairment and plaques in a model of Alzheimer's disease. Nature. 2000; 408:979-82.

Jhamandas J H, MacTavish D. Antagonist of the Amylin Receptor Blocks β-Amyloid Toxicity in Rat Cholinergic Basal Forebrain Neurons. J Neurosci. 2004; 24:5579-84.

Jhamandas J H, Li Z, Westaway D, Yang J, Jassar S, MacTavish D. Actions of β-Amyloid Protein on Human Neurons Are Expressed through the Amylin Receptor. Am J Pathol. 2011; 178:140-9.

Jhamandas J H M D. β-Amyloid protein (Aβ) and human amylin regulation of apoptotic genes occurs through the amylin receptor. Apoptosis. 2012; 17:37-47.

Jhamandas J H V V, MacTavish D, Fu W Microglial amylin receptors: a novel target for the actions of beta amyloid (Aβ) protein. Society for Neuroscience Meeting Abstracts 39.01/B88, Chicago, Ill. USA. 2015.

Kimura R, MacTavish D, Yang J, Westaway D, Jhamandas J H. Beta Amyloid-Induced Depression of Hippocampal Long-Term Potentiation Is Mediated through the Amylin Receptor. J Neurosci. 2012; 32:17401-6.

Kimura R M D, Yang J, Westaway D, Jhamandas J H. Pramlintide Antagonizes Beta Amyloid (Aβ)- and Human Amylin-Induced Depression of Hippocampal Long-Term Potentiation. Mol Neurobiol. 2016. Jan. 15. [Epub ahead of print]

Liu Y-H, Giunta B, Zhou H-D, Tan J, Wang Y-J. Immunotherapy for Alzheimer disease: the challenge of adverse effects. Nat Rev Neurol. 2012; 8:465-9.

Patel A N, Jhamandas J H. Neuronal receptors as targets for the action of amyloid-beta protein (Aβ) in the brain. Expert Rev Mol Med. 2012; 14: 14:e2. doi: 10.1017/S1462399411002134.

Roth J D. Amylin and the regulation of appetite and adiposity: recent advances in receptor signaling, neurobiology and pharmacology. Curr Opin Endocrinol Diabetes Obes. 2013; 20:8-13.

Selkoe D J. Normal and Abnormal Biology of the beta-Amyloid Precursor Protein. Annu Rev of Neurosci. 1994; 17:489-517.

Selkoe D J. The therapeutics of Alzheimer's disease: Where we stand and where we are heading. Ann of Neurol. 2013; 74:328-36.

Vassar R. BACE1 inhibitor drugs in clinical trials for Alzheimer's disease. Alzheimer's Res Ther. 2014; 6:1-14.

Wang H, Abedini A, Ruzsicska B, Raleigh D P. Rationally Designed, Nontoxic, Nonamyloidogenic Analogues of Human Islet Amyloid Polypeptide with Improved Solubility. Biochemistry. 2014; 53:5876-84.

Westermark P, Andersson A, Westermark G T. Islet Amyloid Polypeptide, Islet Amyloid, and Diabetes Mellitus. Physiol Rev. 2011; 91:795-826.

Wu H, Yao L, Mei J, Li F. Development of synthetic of peptide-functionalized liposome for enhanced targeted ovarian carcinoma therapy. Int J Clin Exp Pathol. 2015; 8:207-16. www.alzheimers.net/resources/alzheimers-statistics. 2016.

Zhu H, Wang X, Wallack M, Li H, Carreras I, Dedeoglu A, et al. Intraperitoneal injection of the pancreatic peptide amylin potently reduces behavioral impairment and brain amyloid pathology in murine models of Alzheimer's disease. Mol Psychiatry. 2015; 20:252-62.

What is claimed is:

1. An amylin receptor antagonist selected from the group consisting of cyclic AC253 having the amino acid sequence of SEQ ID NO: 2 and a peptide fragment of AC253 consisting of an amino acid sequence selected from the group consisting of SEQ ID NO: 3, 4, 5, 6, 7, 8, 9, 10, 11, 12, 13, 14, 15, and 16, wherein the amylin receptor antagonist is brain penetrant and capable of binding to an amylin receptor and inhibiting activity of amylin, amyloid-beta protein, or both.

2. The amylin receptor antagonist of claim 1, wherein the amylin receptor antagonist is the peptide fragment and the amino acid sequence is SEQ ID NO: 7, and wherein the amylin receptor antagonist is capable of binding to amylin subtype 1 (AMY1) and amylin subtype 3 (AMY3) receptors.

3. The amylin receptor antagonist of claim 1, wherein the amylin receptor antagonist is the peptide fragment and the amino acid sequence is SEQ ID NO: 12, and wherein the amylin receptor antagonist is capable of binding to AMY1 receptor.

4. The amylin receptor antagonist of claim 1, wherein the amylin receptor antagonist is the peptide fragment and the amino acid sequence is SEQ ID NO: 16, and wherein the amylin receptor antagonist is capable of binding to AMY1 and AMY3 receptors.

5. A composition or pharmaceutical composition comprising the amylin receptor antagonist of claim 1, and a pharmaceutically acceptable carrier.

* * * * *